United States Patent
Yoo et al.

(10) Patent No.: US 10,952,608 B2
(45) Date of Patent: Mar. 23, 2021

(54) PERFORMING A PROCEDURE BASED ON MONITORED PROPERTIES OF BIOLOGICAL TISSUES

(71) Applicants: The General Hospital Corporation, Boston, MA (US); Intelon Optics, Inc., Los Angeles, CA (US)

(72) Inventors: Jang Lawrence Hyun Yoo, Los Angeles, CA (US); Dominik Jean Michel Beck, Muttenz (CH); Giuliano Scarcelli, Washington, DC (US); Niaz Karim, Weston, MA (US); Seok-Hyun Yun, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/548,264

(22) PCT Filed: Sep. 2, 2016

(86) PCT No.: PCT/US2016/050147
§ 371 (c)(1),
(2) Date: Aug. 2, 2017

(87) PCT Pub. No.: WO2017/040959
PCT Pub. Date: Mar. 9, 2017

(65) Prior Publication Data
US 2018/0160898 A1    Jun. 14, 2018

Related U.S. Application Data

(60) Provisional application No. 62/213,423, filed on Sep. 2, 2015.

(51) Int. Cl.
*A61B 3/103*    (2006.01)
*A61B 3/10*    (2006.01)
(Continued)

(52) U.S. Cl.
CPC .............. *A61B 3/103* (2013.01); *A61B 3/10* (2013.01); *A61B 3/1005* (2013.01);
(Continued)

(58) Field of Classification Search
CPC ...... G01J 3/44; G01J 3/4412; G02B 27/0093; A61F 9/007; A61F 9/00736; A61F 9/008;
(Continued)

(56) References Cited

U.S. PATENT DOCUMENTS

2009/0171305 A1    7/2009  El Hage
2009/0323056 A1   12/2009  Yun
(Continued)

FOREIGN PATENT DOCUMENTS

WO    WO2009039302 A2    3/2009
WO    WO2012149570 A1   11/2012
WO    WO20120162529 A1  11/2012

OTHER PUBLICATIONS

International Search Report and Written Opinion for International Application No. PCT/US2016/050147 dated Dec. 8, 2016, 14 pages.
(Continued)

*Primary Examiner* — Nicholas R. Pasko
(74) *Attorney, Agent, or Firm* — Quarles & Brady LLP

(57) ABSTRACT

A procedure is performed on at least one section of an ocular component. At least one first electro-magnetic radiation is provided to the section so as to interact with at least one acoustic wave in the ocular component. At least one second electro-magnetic radiation is produced based on the interaction. Multiple portions of the second electromagnetic radiation are received. Each portion was emitted from a different corresponding segment of the section. A viscoelastic modulus of the section is monitored based on the multiple portions during the procedure. Feedback is applied
(Continued)

to the procedure based at least in part on the monitored visco-elastic modulus, including at least one of: (1) guiding a trajectory of an incision based on different respective monitored values of visco-elastic modulus for the segments, or (2) determining a number of incisions to be made based on different respective monitored values of visco-elastic modulus for the segments.

28 Claims, 9 Drawing Sheets

(51) Int. Cl.
- *A61B 5/00* (2006.01)
- *G01J 3/44* (2006.01)
- *A61B 3/16* (2006.01)

(52) U.S. Cl.
CPC .......... *A61B 5/0075* (2013.01); *G01J 3/4412* (2013.01); *A61B 3/102* (2013.01); *A61B 3/16* (2013.01)

(58) Field of Classification Search
CPC .............. A61F 9/00802; A61F 9/00825; A61F 9/00827; A61F 2009/00844; A61F 2009/00846; A61F 2009/00853; A61F 2009/00861; A61F 2009/00865; A61F 2009/0087; A61F 2009/00872; A61F 2009/00887; A61F 2009/00889; A61B 3/00; A61B 3/1025; A61B 3/103; A61B 3/14; A61B 3/152; A61B 3/16; A61B 3/165; A61B 3/0025; A61B 3/10; A61B 3/1005; A61B 3/102; A61B 3/107; A61B 3/1173; A61B 5/00; A61B 5/0059; A61B 5/0062; A61B 5/0093; A61B 5/0068; A61B 5/0075; A61B 5/0095; A61B 5/0097

USPC ........ 351/200, 205, 206, 221, 246; 356/301, 356/326; 600/300, 398, 407, 476; 606/1, 606/2, 4, 6

See application file for complete search history.

(56) References Cited

U.S. PATENT DOCUMENTS

| | | |
|---|---|---|
| 2011/0237999 A1 | 9/2011 | Muller |
| 2012/0215155 A1* | 8/2012 | Muller .................. A61N 5/062 604/20 |
| 2012/0302862 A1* | 11/2012 | Yun ...................... A61B 5/0068 600/398 |
| 2012/0303008 A1* | 11/2012 | Muller ................ A61F 9/00836 606/5 |
| 2014/0316388 A1* | 10/2014 | Hipsley ............... A61F 9/00802 606/4 |
| 2014/0368793 A1* | 12/2014 | Friedman ................. A61B 3/10 351/206 |

OTHER PUBLICATIONS

China National Intellectual Property Administration, First Office Action for application 201680050800.1, dated Oct. 21, 2019, with translation.

European Patent Office, Examination Report for application 16779205.0, dated Mar. 20, 2019.

European Patent Office, Extended European Search Report and European Search Opinion for application 12775982.7, dated Nov. 6, 2014.

Scarcelli, G. et al. "Brillouin microscopy for ocular biomechanics." Conference on Lasers and Electro-Optics. Optical Society of America, 2010.

Scarcelli, G. et al. "Confocal Brillouin microscopy for three-dimensional mechanical imaging." Nature photonics 2.1 (2008): 39.

\* cited by examiner

PERFORMING A PROCEDURE BASED ON MONITORED PROPERTIES OF BIOLOGICAL TISSUES

CROSS-REFERENCE TO RELATED APPLICATIONS

This application is a U.S. National Phase of PCT Application No. PCT/US2016/050147 filed on Sep. 2, 2016, 2016, which claims the benefit of U.S. Provisional Application No. 62/213,423 filed Sep. 2, 2015, incorporated herein by reference.

This application is related to, but does not claim priority to, U.S. application Ser. No. 13/460,595, filed Apr. 30, 2012, and U.S. Patent Application No. 61/480,885, filed Apr. 29, 2011, each of which is incorporated herein by reference.

BACKGROUND

This description relates to performing a procedure based on monitored properties of biological tissues.

Although Brillouin spectroscopy has been used for material characterization, various issues have limited its use for imaging biological tissues in certain contexts (e.g., in vivo imaging).

SUMMARY

In one aspect, in general, a method for performing a procedure based on monitored properties of at least one ocular component of an eye includes: performing a procedure on at least one section of a first ocular component of the eye; providing at, least one first electro-magnetic radiation to the at least one section of the first ocular component so as to interact with at least one acoustic wave in the first ocular component, wherein at least one second electro-magnetic radiation is produced based on the interaction; receiving multiple portions of the at least one second electro-magnetic radiation, each portion having been emitted from a different corresponding segment of the at least one section of the first ocular component; monitoring a visco-elastic modulus of the at least one section of the first ocular component based on the multiple portions during the procedure performed on the at least one section of the first ocular component; and applying feedback to the procedure based at least in part on the monitored visco-elastic modulus, including at least one of: (1) guiding a trajectory of an incision based on different respective monitored values of visco-elastic modulus for the segments, or (2) determining a number of incisions to be made based on different respective monitored values of visco-elastic modulus for the segments.

Aspects can include one or more of the following features.

The procedure comprises a procedure that increases stiffness of the first ocular component.

The procedure that increases stiffness of the first ocular component comprises collagen crosslinking of a cornea of the eye.

The procedure comprises a procedure that reduces stiffness of the first ocular component.

The procedure that reduces stiffness of the first ocular component comprises an incision.

Applying feedback to the procedure based at least in part on the monitored visco-elastic modulus includes guiding a trajectory of the incision based on different respective monitored values of visco-elastic modulus for the segments.

Guiding the trajectory includes determining at least one of: a radius of curvature of at least a portion of the trajectory, or a length of the trajectory.

Applying feedback to the procedure based at least in part on the monitored visco-elastic modulus includes determining a number of incisions to be made based on different respective monitored values of visco-elastic modulus for the segments.

The incision comprises a laser incision that induces optical breakdown of the first ocular component based on cavitation bubble creation.

The incision comprises a mechanical incision that induces mechanical breakdown of the first ocular component.

The first ocular component comprises a crystalline lens of the eye, and the procedure that reduces stiffness of the first ocular component comprises laser induced optical breakdown of the crystalline lens.

The procedure uses an optical source to provide a third electro-magnetic radiation to the at least one section of the first ocular component.

The procedure uses an acoustic source to provide at least a portion of the energy in the acoustic wave.

The at least one second electro-magnetic radiation is produced based on a Brillouin scattering interaction.

Applying feedback to the procedure includes applying real time feedback to guide the procedure in real time.

Guiding the procedure in real time includes determining a plurality of values of visco-elastic modulus for the segments based on different respective values of a spectral characteristic of each of the multiple portions of the at least one second electro-magnetic radiation in less than 0.4 seconds.

Applying feedback to the procedure includes guiding the procedure over the at least one section based on different respective monitored values of visco-elastic modulus for the segments.

The segments are distributed in three spatial dimensions to provide anisotropic monitoring of the visco-elastic modulus.

A monitored value of visco-elastic modulus for each of multiple segments is computed based on a numerical analysis that provides a time-dependent evolution of a spatial-dependent function of multiple discrete element values, where each discrete element value is derived from a monitored value of visco-elastic modulus for at least one of the multiple segments, and each discrete element value is updated at each of multiple sequential times during the procedure.

The numerical analysis comprises finite element analysis.

A monitored value of visco-elastic modulus for a particular segment is determined based at least in part on at least one of a spectral line width or spectral shift of a spectrum of a corresponding portion of the at least one second electro-magnetic radiation.

The method further includes: performing the procedure on at least one section of a second ocular component of the eye; providing, a portion of the at least one first electro-magnetic radiation to the at least one section of the second ocular component so as to interact with at least one acoustic wave in the second ocular component, wherein at least one third electro-magnetic radiation is produced based on the interaction; receiving multiple portions of the at least one third electro-magnetic radiation, each portion having been emitted from a different corresponding segment of the at least one section of the second ocular component; monitoring a visco-elastic modulus of the at least one section of the second ocular component based on the multiple portions of the at least one third electro-magnetic radiation during, the procedure performed on the at least one section of the second ocular component; and applying feedback to the procedure based at least in part on the monitored visco-elastic modulus of the at least one section of the second ocular component; wherein the multiple portions of the at least one second electro-magnetic radiation are received through a spectrometer configured to have a first extinction efficiency that isolates a spectral characteristic of the at least one second electro-magnetic radiation, and the multiple portions of the at least one third electro-magnetic radiation are received through the spectrometer configured to have a second extinction efficiency that isolates a spectral characteristic of the at least one third electro-magnetic radiation.

The second extinction efficiency is greater than the first extinction efficiency, the number of received portions of the at least one third electro-magnetic radiation is lower than the number of received portions of the at least one second electro-magnetic radiation, and the time over which each portion of the at least one third electro-magnetic radiation is received is longer time over which each portion of the at least one second electro-magnetic radiation is received.

The first ocular component is a cornea of the eye, and the second ocular component is a sclera of the eye.

Monitoring the visco-elastic modulus of the at least one section of the first ocular component includes detecting the portions of the at least one second electro-magnetic radiation using a polarization sensitive device to determine characteristics of the portions of the at least one second electro-magnetic radiation that are associated with propagation direction of the acoustic wave.

Monitoring the visco-elastic modulus of the at least one section of the first ocular component includes detecting each of the portions of the at least one second electro-magnetic radiation in a different location of a two-dimensional sensor array.

The visco-elastic modulus is determined for each of a plurality of the segments, and is represented a parameter that includes a component representing a viscous modulus and a component representing an elastic modulus.

In another aspect, in general, an apparatus for performing a procedure based on monitored properties of at least one ocular component of an eye includes: at least one first arrangement configured to perform a procedure on at least one section or a first ocular component of the eye; at least one second arrangement configured to provide at least one first electro-magnetic radiation to the at least one section of the first ocular component so as to interact with at least one acoustic wave in the first ocular component, wherein at least one second electro-magnetic radiation is produced based on the interaction; at least one third arrangement configured to receive multiple portions of the at least one second electro-magnetic radiation, each portion having been emitted from a different corresponding segment of the at least one section of the first ocular component; and at least one fourth arrangement configured to monitor a visco-elastic modulus of the at least one section of the first ocular component based on the multiple portions during the procedure performed on the at least one section of the first ocular component; wherein the first arrangement is further configured to apply feedback to the procedure based at least in part on the monitored visco-elastic modulus, including at least one of: (1) guiding a trajectory of an incision based on different respective monitored values of visco-elastic modulus for the segments, or (2) determining a number of incisions to be made based on different respective monitored values of visco-elastic modulus for the segments.

In other aspects, in general, apparatus and methods are capable of providing biomechanical information about at least one portion of ocular tissues in patients or animals in vivo with spatial resolution. Brillouin light scattering generated from within the tissues in the eye is used to obtain the biomechanical information of the tissues. The spectral characteristics of the scattered light is analyzed and processed to provide the biomechanical information relevant to the health and illness of the ocular tissues, such as the weakening of the corneal stroma or age-related stiffening of the nucleus in the crystalline lens. A probe beam is scanned across the tissue to obtain one, two, or three-dimensional spectral data of Brillouin scattered light. The obtained information is displayed in the form of images or parameters derived from the measured spectral characteristics.

Aspects can have one or more of the following advantages.

The techniques described herein relate to arrangements and methods to obtain the biomechanical and physiological properties of ocular components, including various ocular tissues and/or structures, such as the cornea, sclera, and crystalline lens, in the eye of a patient or a living animal to perform procedures for diagnosis and/or treatment of ocular disorders, as well as basic study and preclinical developments. The information is obtained from the spectral analysis of Brillouin light scattering that is associated with the hypersonic acoustic properties in the ocular components.

The techniques enable noninvasive interrogation of the biomechanical information that is relevant to and useful in diagnosing, ocular disorders, such as corneal ectasia and presbyopia, as well as treating these problems. Thus, a quantitative approach is provided for screening refractive surgery patients, identifying candidates at risk, and optimizing ablation patterns.

By using Brillouin scattering spectroscopy to monitor a visco-elastic modulus of an ocular tissue during a procedure, that procedure can be guided in real time using feedback from the monitored visco-elastic modulus. The monitored visco-elastic modulus can provide a measurement of biomechanical changes caused by cellular processes associated with procedures such as surgical procedures or other types of treatment procedures. Biomechanical changes to an ocular component (or other biological tissue) may include changes that affect their cellular structures (e.g., extracellular matrix, collagen fibers, astrocytes, keratocytes, etc.).

Compared to other techniques for modeling ocular structures using numerical analysis (such as finite element analysis), which may be required to use inverse modeling to account for such characteristics as intra-ocular pressure (IOP), the techniques described herein enable direct mapping of visco-elastic modulus in the context of many material characteristics, including IOP, without the need to necessarily perform additional computational steps, such as inverse modeling.

Other features and advantages of the invention will become apparent from the following description, and from the claims.

DESCRIPTION

Figure 1A:
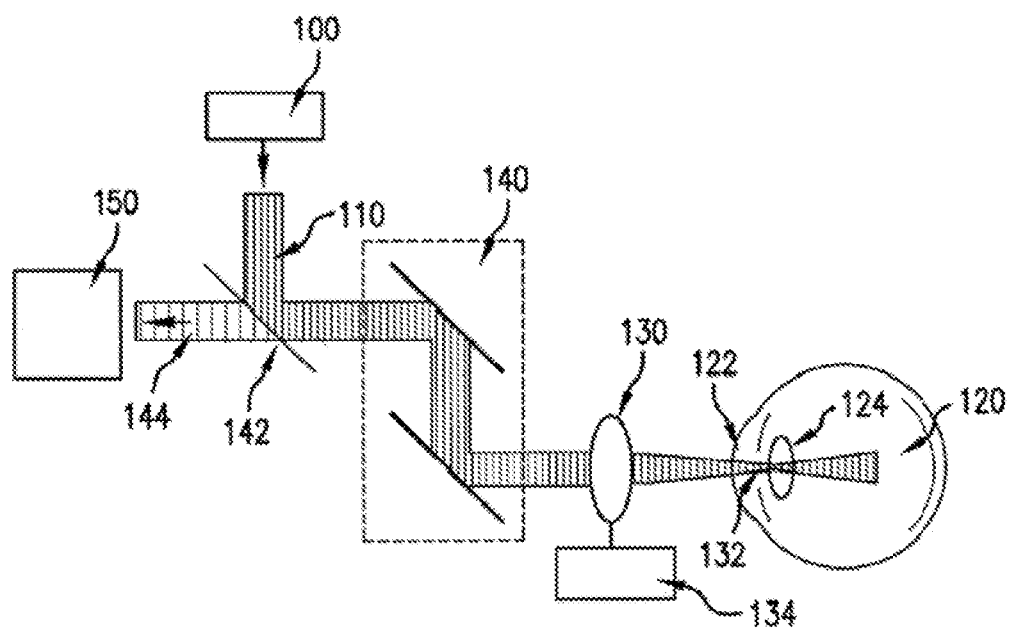
FIG. 1A is a schematic of an exemplary embodiment of the Brillouin ocular analyzer.

It has long been known that the lens tends to stiffen with age. As the lens becomes hard, the muscle holding the lens cannot alter its shape easily, and the person has increasing difficulty focusing on close objects or loss of accommodation ability, a condition called presbyopia. Presbyopia affects almost every person over the age of 45. Nevertheless, clinicians do not have tools to characterize the biomechanical alterations in the lens. Furthermore, no drugs are available that can prevent, slow, or reverse the progressive nature of this condition.

Cataract, opacity of the lens, is the leading cause of blindness in the world. Age-related nuclear cataract is the most common form, affecting more than 50% of U.S. residents 65 and older. Despite its prevalence, the only standard of care for cataract patients today is surgery, an invasive procedure, which is usually performed after patients have suffered from deteriorating vision for many years before they are eligible for the procedure. About 1.5 million people in the U.S. (of the 87 million with cataracts) receive cataract surgery annually, leaving more than 85 million people untreated for this condition. A drug that can treat or prevent the damage of the lens proteins is being actively sought for. However, our limited understanding of the mechanisms of cataracts and the dearth of techniques capable of monitoring the genesis of cataracts had impeded the drug development. Although the detailed mechanisms underlying the cataract formation remain to be further elucidated, it has been known that the opacity of the lens can result from the denaturation of lens proteins. This structural and physiological modification can alter the lens's elastic properties. Therefore, the ability to measure lens elasticity in patients may be useful for early diagnosis and development of non-surgical interventions for cataracts.

In the cornea, the mechanical balance between corneal stiffness and intraocular pressure is critical in maintaining the appropriate shape and normal function of cornea. An abnormal change in the mechanical properties of the cornea can therefore degrade visual acuity and threaten vision. Corneal ectasia refers to a bulging of the cornea, occurring when it is not strong enough mechanically to withstand the intraocular pressure. Ectasia may result from a degenerative disease called Keratoconus. Keratoconus and Keratoectasia occur in 1 out of 1000 people among the general population and are often a complication of LASIK surgery performed in 1.5 million patients in the USA each year. All of these conditions and procedures are intrinsically linked to ocular mechanical properties, and from a diagnostic standpoint are expected to alter, at a very early stage, the mechanical properties of ocular tissues.

Ectasia is also one of the rare but serious adverse outcomes after LASIK (laser-assisted in situ keratomileusis) surgery. Currently about 1.5 million LASIK operations are performed annually in the U.S. As LASIK becomes increasingly popular, the incidence of post-LASIK ectasia has continued to increase. A promising therapeutic approach to corneal ectasia is increasing the stiffness of the stroma by crosslinking the naturally present collagen fibers in the cornea, a procedure known as corneal collagen crosslinking (CXL). The viscoelastic properties of the cornea are also known to affect the tonometry measurement of intraocular pressure.

As a consequence, the biomechanical properties may be an appropriate target for diagnosis and monitoring of onset and progression of cataract and refractive disorders such as myopia, hyperopia, astigmatism, and presbyopia as well as corneal pathologies and treatments. For this reason, there has been a great deal of interest in measuring the mechanical properties of the lens, scleral, and corneal tissues for diagnosis and for monitoring of treatments. However, current techniques cannot detect such localized biomechanical changes in vivo in patients and animal models, seriously frustrating our efforts to develop understanding and treatment of the prevalent ocular problems.

Conventional techniques, from the traditional slit-lamp microscopy to newer imaging technologies (computer videokeratography, OCT, confocal microscopy, ultrasound, Scheimflug photography) are excellent in imaging the structure of cornea, sclera, conjunctiva, and crystalline lens but fail to provide their physiological and biomechanical information. Current clinical instruments, such as pachymetry (measuring thickness) and topography (mapping surface curvature), have been limited in screening patients at high risk of post-LASIK ectasia; patients with normal appearing corneas have developed the complication.

Several techniques have been used to characterize the mechanical properties of the cornea, sclera and lens ex vivo and in vivo. For example, comprehensive but destructive analysis has been performed by spinning cup, mechanical stretchers, stress-strain equipment or by inflation tests. Other mechanical testing methods include laser induced optical breakdown based on bubble creation and the ocular response analyze measuring corneal hysteresis on the surface without spatial information. Ultrasound is an attractive tool as it allows noninvasive methods such as elastography. Of particular note is ultrasound pulse-echo techniques and ultrasound spectroscopy, where pulsed or continuous-wave acoustic waves are launched onto the cornea, and the propagation speed and attenuation are measured to compute the viscoelastic moduli of the tissue. However, the ultrasound-based techniques have drawbacks of relatively low spatial resolution and measurement sensitivity.

Brillouin light scattering in a tissue or any other medium arises due to the interaction between an incident light and acoustic waves within the matter. Consider a probe light with a frequency v and a wavelength λ, which is illuminated to the sample. In spontaneous Brillouin process, the acoustic waves or acoustic phonons are naturally present due to thermal fluctuations. Such fluctuations propagate through the medium in the form of acoustic waves. These acoustic waves generate periodic modulations of the refractive index. Brillouin scattering can be generated by at least one or many acoustic waves or acoustic phonons, which form phase-matched index modulation.

FIG. 1A illustrates an exemplary embodiment of the description. A first arrangement 100 provides a first electromagnetic radiation 110, which is delivered to an eye 120. A most appropriate form of the electromagnetic radiation 110 is light in the visible or near infrared range. The first arrangement includes a light source, which is typically a single-frequency laser, a filtered Mercury lamp, or other types of light emitters known in the art. The light source can have a wavelength between 530 nm and 1350 nm, but other wavelengths that are known to be safe for use in the eye can be used. The linewidth of the light is typically less than 1 GHz or more preferably less than 100 MHz, but light sources with broader linewidth or multiple spectral lines may be used in conjunction with appropriate arrangements.

The electromagnetic radiation 110 is directed to the eye 120 to probe various portions of ocular tissues, including but not limited to the cornea 122 and the crystalline lens 124. In general, an imaging lens 120 is used to focus the electromagnetic radiation 110 onto a small spot. The imaging lens 120 can be a spherical convex lens, aspheric lens, objective, lens, theta lens, or cylindrical lens for line focusing.

To scan the axial position of the focus within the ocular tissues, the imagining lens 130 may be mounted on a translation stage 134. Alternatively, a tunable element that changes the divergence of the probe light may be employed. To scan the transverse position of the focus, a one or two-axis beam scanner 140 is employed. The scanner 140 can be a galvanometer-mounted mirror, MEMS mirror, translation stages, or spatial light modulator.

The acousto-optic interaction in the tissue gives rise to light scattering, generating second electromagnetic radiation. Several mechanisms for light scattering are known in the art, which includes Rayleigh and Mie scattering, Raman scattering, and Brillouin scattering. While in general biological tissues support all of these scattering mechanisms, Brillouin scattering is directly associated with the acoustic waves in the medium. A portion of the at least one second electromagnetic radiation can be collected by the imaging lens 130. In an epi-detection configuration, the interacting probe and Brillouin-scattered lights travel in the nearly opposite directions. Alternatively, a dual-axis configuration can be employed, where the probe and scattered light for a finite angle.

The system may employ a beam splitter 142 to reflect and transmit the first and second electromagnetic radiations. The beam splitter 142 may have an equal 50/50 splitting ratio or unequal splitting ratios for optimization of the efficiencies of signal generation and collection. The beam splitter 142 may be a neutral splitter with broad spectral bandwidth or a dichroic splitter based on multilayer coating, interference, or diffraction. The portion of the second electromagnetic radiation 144 is sent to a second arrangement 150, which is configured to receive the at least one portion 144 of the at least one second electro-magnetic radiation.

In a preferred embodiment, the second arrangement 150 employs at least one spectral analysis unit, such as a spectrometer, a monochromator, fixed or scanning spectral filters, or other devices known in the art. The second arrangement 150 is configured to measure various properties of the second electromagnetic radiation 144, including but not limited to the center frequency and width of its spectrum, as well as the intensity and polarization of the electrical field. In particular, the frequency difference between the at least one first electromagnetic radiation 110 entering the tissues and the at least one portion of the second electromagnetic radiation 144, which includes the Brillouin scattered light, is of importance.

The frequency shift $v_B$ of the Brillouin scattered light with respect to the probe light 110 is given by $$v_B = \pm \frac{2nV}{\lambda} \sin\left(\frac{\theta}{2}\right) \tag{3}$$

Where n is the local refractive index in the interrogated tissue, V is the speed of the acoustic wave in the sample, and θ is the scattering angle, i.e. the angle between the incident and the scattered light, such as in the dual-axis geometry. In an epi-backward detection configuration, θ=π is a reasonably good approximation. In typical soft tissues, the speed of the acoustic wave ranges from 1000 to 3000 m/s, and the Brillouin frequency shifts are typically between 2 and 20 GHz, depending on the wavelength.

The intrinsic spectral width or linewidth of the Brillouin scattered light is given by:

$$\Delta v_B = \frac{\alpha V}{\pi}, \tag{4}$$

where α is the attenuation coefficient of the acoustic wave in the sample.

The longitudinal complex elastic modulus, M=M'+M", where the real part M' refers to the elastic modulus and the imaginary part M" is the viscous modulus is given by:

$$M'=\rho V^2; \tag{5}$$

$$M''=2\rho V^3 \alpha/v_B. \tag{6}$$

Therefore, the measurement of the spectral characteristics of the Brillouin scattered light provides the information about the biomechanical properties of the ocular tissue. The useful information obtained by the Brillouin measurement includes but is not limited to the acoustic speed, acoustic attenuation coefficient, Brillouin elastic modulus, Brillouin viscous modulus, and electrostriction coefficient. As is further described below, by scanning the focus within the tissue different spatial locations can be probed, which provides the information in a spatially resolved manner. This spatial information can in turn be useful to evaluate for the diagnosis of the mechanical integrity or health of the ocular tissue.

The index of refraction and acoustic speed of a given material are generally dependent on the local temperature and pressure. This dependence may be harnessed for the analysis of inflammatory or pathologic states in the eye via the measurement of the temperature or ph-value in the aqueous and vitreous humors. The magnitude of the Brillouin scattered radiation is related to the coupling of acoustic and optical energy inside the sample, which is related to the material properties, such as the electrostriction coefficient.

Figure 1B:
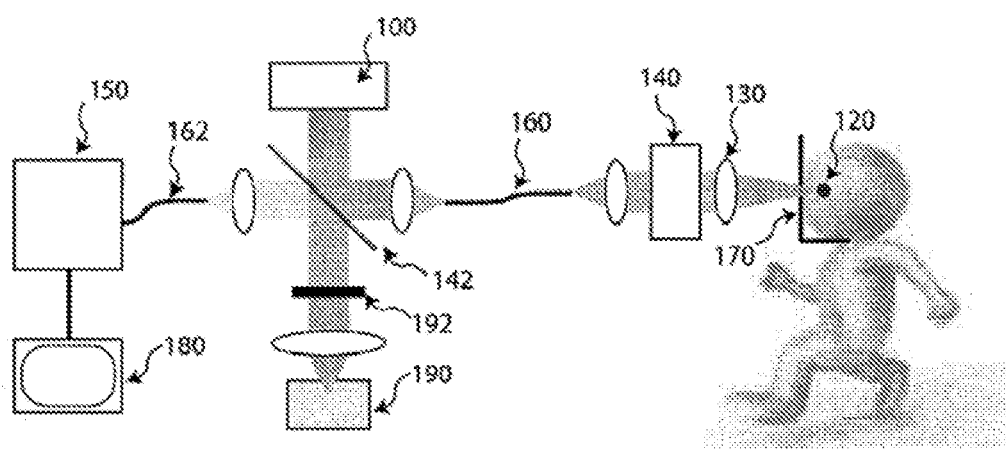
FIG. 1B is a schematic of another exemplary embodiment of the Brillouin ocular analyzer.

FIG. 1B illustrates a modified embodiment that employs an optical fiber 160 between the first arrangement 100 and the beam scanner 140. Another optical fiber 162 can also be used to deliver the Brillouin scattering light to the second arrangement 150. The optical fiber 160 in the sample arm can be preferably a single-mode fiber, but multi-mode, few-mode, or double-clad fibers may be used. Preferably, the optical fiber 182 on the detection arm is a single-mode or few-mode fiber. The optical fiber 162 can serve as a confocal pinhole, allowing the selective collection of essentially only the portion of the second electromagnetic radiation generated from the focus of the probe light in the sample. This confocal detection greatly facilitates the spatially resolved Brillouin measurement with three-dimensional resolution. The principle of confocal detection is well known in the art. Instead of the optical fiber 162, a spatial filter, such as employing a pinhole, may be used. It is desirable to minimize optical reflection at various air-glass or air-tissue interfaces along the beam paths or prevent the reflected light from entering the second arrangement 150 as much as possible.

The system may further comprise a third arrangement 170, which is configured to facilitate positioning the eye 120 with respect to the at least one first electro-magnetic radiation, or the probe light. Preferably, the third arrangement includes at least one of the following features: a forehead rest, a chin rest, an eye fixation beam, and a slit lamp. In particular, the human interface 180 can employ a camera to measure at least one position of the at least one first electro-magnetic radiation with respect to the at least one ocular tissue. This type of beam guiding arrangement can facilitate aiming the probe beam and provide the position information of the focus, which can be used in making of Brillouin images or the spatial map of the biomechanical properties of the ocular tissue.

The system can further comprise a fourth arrangement 180 configured to display the information associated with the at least one portion of the ocular tissue in the eye in vivo. The displayed information may include but is not limited to the Brillouin frequency shifts, Brillouin linewidth, Brillouin images, and the hypersonic viscoelastic moduli, as well as parameters, such as the mean values or slopes, calculated from the Brillouin images or the spatial maps of the viscoelastic properties.

The system arrangement can further employ a fifth arrangement 190 to provide at least one frequency reference. Preferably, the fifth arrangement 190 is configured to receive at least one portion of the first electromagnetic radiation through the beam splitter 142 and reemit Brillouin scattered light with at least one, preferably multiple spectral peaks. For example, the frequency reference 190 comprises at least one reference material, solids or liquids, with known Brillouin frequency shifts. Alternatively, the frequency reference 190 can be a light source emitting an electromagnetic radiation at a wavelength locked to the wavelength of the probe light source 100. In both case, the electromagnetic radiation from the frequency reference 190 is directed to the second arrangement 150. An optical switch 192 can be employed to gate the intensity of the electromagnetic radiation. The reference frequency helps calibrating the spectral analysis unit in the second arrangement 150, facilitating the spectral analysis.

The Brillouin viscoelastic moduli defined in Equations (5) and (6) represent the tissue properties at the hypersonic GHz frequencies. Most soft tissues, including the conical tissues and crystalline lens, exhibit viscoelastic properties characterized by frequency-dependent moduli. Slower relaxation processes have little time to respond to fast mechanical or acoustic modulation, such as GHz acoustic phonons, and thus hardly contribute to the "softness" of the material. As a consequence, modulus tends to increase with frequency, in addition, the propagation of acoustic phonons is governed by the longitudinal modulus, which is typically much higher than the Young's or shear modulus owing to the incompressibility (i.e. Poisson's ratio ~0.5) of water. The two effects, finite relaxation time and low compressibility, provide qualitative explanation for the observed large difference in modulus between the Brillouin and standard mechanical tests.

Figure 2:
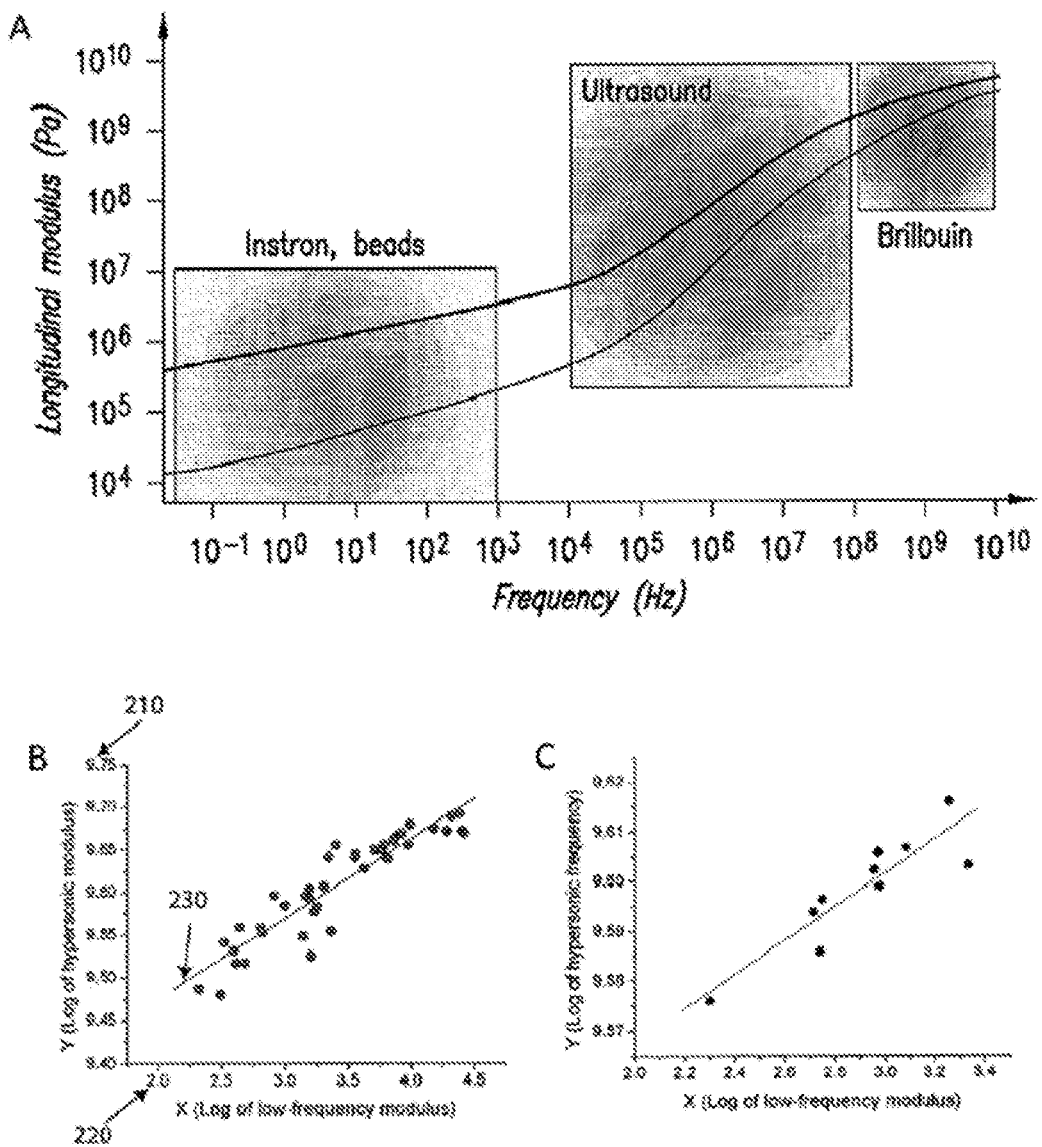
FIGS. 2A-2C illustrate exemplary strategies for scanning the focus of a probe beam for analysis of the human eye.

In one study, we cut fresh porcine and bovine lenses at various ages (from 1 to 18 months) into small pieces of the size our mechanical equipment could handle. The mean Brillouin modulus was calculated from the 3D measurement of Brillouin spectrum and the estimated density and refractive index. As expected, Brillouin-measured elasticity is much higher than the traditional DC elasticity. Nevertheless, there seems to be a clear relationship between Brillouin measurement and standard technique, which shows that the Brillouin signature indeed provides information about the elasticity of lenticular tissue. Comparison to Young's modulus measured by a conventional stress-strain test revealed a remarkable correlation between Brillouin (M') and quasi-static modulus (G') for both porcine and bovine tissues (FIG. 2). High correlation (R>0.9) was obtained in curve fit to a log-log linear relationship: $\log(M')=\alpha \log(G')+b$, where the fitting parameters were $\alpha=0.093$ and $b=9.29$ for porcine tissues and $a=0.034$ and $b=9.50$ for bovine tissues.

Aspects of the techniques described herein make use of Brillouin spectroscopy with optical scanning techniques to guide various procedures. For example, the techniques can be used to characterize features in an eye to guide a procedure involving an incision in that eye (e.g., an incision in a cornea or limbus, or other ocular tissue). For example, some of the characteristics of an incision that can be guided using appropriate feedback include: width, depth, length, curvature, number of incisions, and location of incision(s). Some of the contexts in which this characterization is useful include the following.

1. Incisions, such as Astigmatic Keratotomy (AK) or Limbal Relaxing Incision (LRI) or Arcuate Incision (AI) to correct
    a. Congenital Astigmatism
    b. Residual corneal astigmatism at the time of or following cataract surgery c. Post-traumatic astigmatism
d. Astigmatism after corneal transplantation
e. Astigmatism after a keratorefractive surgical procedure
2. Surgery involving primary incisions to access anterior or posterior chambers of the eye (e.g., Cataract surgery)
   a. Primary incision to access the anterior or posterior chambers of the eye (e.g., a Limbal Incision, Corneal Inscision, or Scleral Inscision)
   b. Secondary incision –AK (LRI or AI) that corrects induced+existing astigmatism
      i. Penetrating incision (e.g., Cut in cornea made from anterior surface including epithelial layer)
      ii. Intra-stromal incision (e.g., Cut made within stroma layer, such as cuts for: small incision lenticula extraction (SMILE), pockets, guiding planes, access ports, etc.)
3. Surgery involving access to the crystalline lens (e.g., Presbyopia surgery) and creation of gliding planes for softening of the crystalline lens AK, which includes LRI or AI, is a surgical procedure used to treat congenital astigmatism, residual corneal astigmatism at the time of or following cataract surgery, post-traumatic astigmatism and astigmatism after corneal transplantation.

In the case of cataract surgery, a primary incision is made to enable access to crystalline lens and intraocular lens, and a secondary incision or multiple incisions (AK) are made in the cornea to change the refraction to correct astigmatism, both pre-existing and that which may have been induced by the primary incision. Two examples of AK incisions are those that are penetrating, which cut into the stroma layer through the epithelial layer and those that are intra-stromal, which only disrupt the stromal part of the cornea by using an energy source (e.g., a femtosecond laser) or a mechanical instrument (e.g., knives or blades formed from steel, diamond, etc.). The techniques described herein are not limited to only AKs, but may apply to other corneal keratoplasties that include incisions, such as radial keratotomies, or apply thermal energy, mechanical energy or chemical cross-linking to change the shape of the cornea.

Surgical planning for AKs assess a combination of patient data including patient age, refractive history, conical topography, pachymetry, and other imaging (e.g., optical coherence tomography (OCT), wavefront aberrometry, keratometry, and/or corneal and anterior chamber raytracing) findings in order to conic up with appropriate nomogram selection to guide the nature of the incision, including incision length, depth, uniformity of depth, angle and location. Nomograms are typically used in conjunction with surgical systems such as femtosecond lasers, if done manually, AKs are typically placed based on surgeon's experience. AK planning may be done in both cases. In the techniques described herein, a Brillouin modulus value or 2D or 3D Brillouin maps of Brillouin modulus values within the cornea (e.g., modulus maps of the mid-peripheral and peripheral areas) are created to provide guidance for the location and characteristics of an incision that may have a variety of objectives, including minimizing surgically induced astigmatism (SIA), correcting existing astigmatism in the eye, or other procedures that use incisions to change the cornea's refractive properties. For example, depending on the mechanical status, such as the modulus or stress, in the location where the incision is made on cornea or corneal limbus, or possibly sclera, it is expected that the outcome, e.g. change in astigmatism, will be different. In one embodiment, one or multiple measurements of the corneal modulus and/or scleral modulus can be completed at set depths or/and intervals, which may include specific ratios (e.g., thickness of the cornea/desired # of measurements) or patterns (e.g., modulus measurements taken at equidistant points through the depth of the cornea), to optimize mapping of modulus gradients in the cornea. Also the limbal region can be included in the measurements as the "hinge" zone (transitional zone) between two mechanically different tissue structures (rigid sclera and more compliant cornea or vice versa).

In case of softening of the crystalline lens, one or multiple intra-lenticular incisions are made to create gliding planes or cut lines. This is expected to reduce the bulk stiffness of the lens to make it softer so it can alter its shape while accommodating and increase its refractive power by enlarging the exterior surface curvature.

In some embodiments, the spectrometer used to isolate the Brillouin spectral characteristic the characteristic from which the visco-elastic modulus is derived) has a configurable spectral efficiency. An example of such a spectrometer, described in more detail below, uses as configurable number of VIPA stages to change the extinction efficiency. Some ocular components scatter more light and require a higher extinction efficiency in order to filter out enough noise to achieve a satisfactory signal-to-noise ratio. But, a higher extinction efficiency also calls for a longer time to collect the Brillouin generated light (e.g., using a lone integration time in a charge coupled device (CCD) detector). That longer collection time for each CCD line means there are fewer distinct mapping locations that can be scanned in a given time period, and therefore a lower mapping resolution that can be acquired in the time period (which may be as short as 0.4 second, for example, for real time operation). So, there is a trade-off between extinction efficiency and mapping resolution. But, for certain ocular components, such as the sclera, a lower mapping resolution (than a resolution of for the cornea, for example) is acceptable. Any of a variety of detectors may be used as a two-dimensional sensor array other than, or in addition to, a CCD detector (e.g., CMOS, sCMOS, EMCCDs, etc.).

There may be specific locations (e.g., points, zones, regions, layers, areas) within an ocular component, such as the cornea or sclera, (e.g., in Z-axis) that represent the stiffness profile most efficiently. A variety of different types of biomechanical heat maps of an ocular component can be generated by measuring equidistantly, for example, or by concentrating measurements in certain areas. For example, maps may cover various distributions of measurement concentration through the thickness of the ocular component.

FIG. 2 show various examples illustrating how the focus 132 is scanned over the eye 120 to obtain the biomechanical information at multiple locations in ocular tissues and thereby to obtain Brillouin images. Various scan types are known in the art, which includes axial line scan, lateral line scan, raster area scan, three-dimensional scan, and random sampling scan.

In one example, the focus of the probe light is positioned at a center of the cornea or the lens. When this on-axis focus 200 is scanned along the depth coordinate (i.e. Z axis), an axial profile of the biomechanical information, or Brillouin axial profile, is obtained. An off-axis axial profile is obtained by using an off-axis focus 210 displaced from the optic axis of the cornea or the crystalline lens. For corneal scan, far-off-axis focus 220 can be used, in which case the iris blocks the probe light from entering the crystalline lens.

In another examples, lateral line-scan or 2-dimensional cross-sectional scan is achieved by moving a focus along a linear trace 230. A 2-dimensional en face or 3-dimensional scan can be achieved by moving the focus over an area in the X and V coordinates. A simple raster scan 240 or hexagonal scan 250 may be used.

In epi-confocal detection, the axial and lateral span of the focus determines the axial and lateral resolution of Brillouin imaging, which is given by the numerical aperture (NA) of the imaging lens 120. For a given NA, the axial resolution is higher in a dual-axis configuration than the backward epi detection. Appropriate NA for probing the cornea and crystalline lens typically ranges from 0.1 to 0.9. For retinal examination, the imaging lens 120 may not be employed, as the crystalline lens itself can focus the probe beam onto the retina.

Thermal damage by optical absorption in the cornea, lens, and retina is one of the primary considerations in eye safety. The maximum light exposure level to the eye is relatively well known in the literature. An optimal power level, of the probe light should be used for eye safety as well as for maximal signal-to-noise ratio. For example, for a wavelength of 780 nm, approximately 0.5 to 3 mW of continuous-wave power may be allowed for corneal and lens examinations.

The spectral analysis unit in the second arrangement 150 should have a high spectral resolution, a high sensitivity and a high extinction. This relatively low illumination power and the relatively low cross-section of Brillouin scattering place a stringent requirement on the sensitivity of the spectral unit employed in the second arrangement 150. This places a stringent requirement on the extinction of the spectral analysis unit.

As a spectral analysis unit, a scanning Fabry-Perot interferometer may be used. The interferometer may be designed to have a free spectral range of about 50 GHz and finesse of about 1,000 with either a single-pass or a multi-pass configuration. Another alternative spectral analysis unit is a fixed spectral filter with a bandpass, notch or edge type. Which measures the magnitude of a certain frequency component. In this case, the optical frequency of the first electromagnetic radiation may be stabilized or locked with respect to the fixed filter. Other possible embodiment for the second arrangement 150 includes heterodyne detection based on the beating between the probe and Brillouin scattered light.

One of the preferred embodiments for the spectral unit is a spectrometer employing at least one virtually imaged phased array (VIPA) etalon. A VIPA 300 disperses the spectrum of input light into different angles or spatial points. A conventional VIPA with uniform reflectance coatings has an extinction ratio of about 30 dB in its spectral transfer function.

Figure 3:
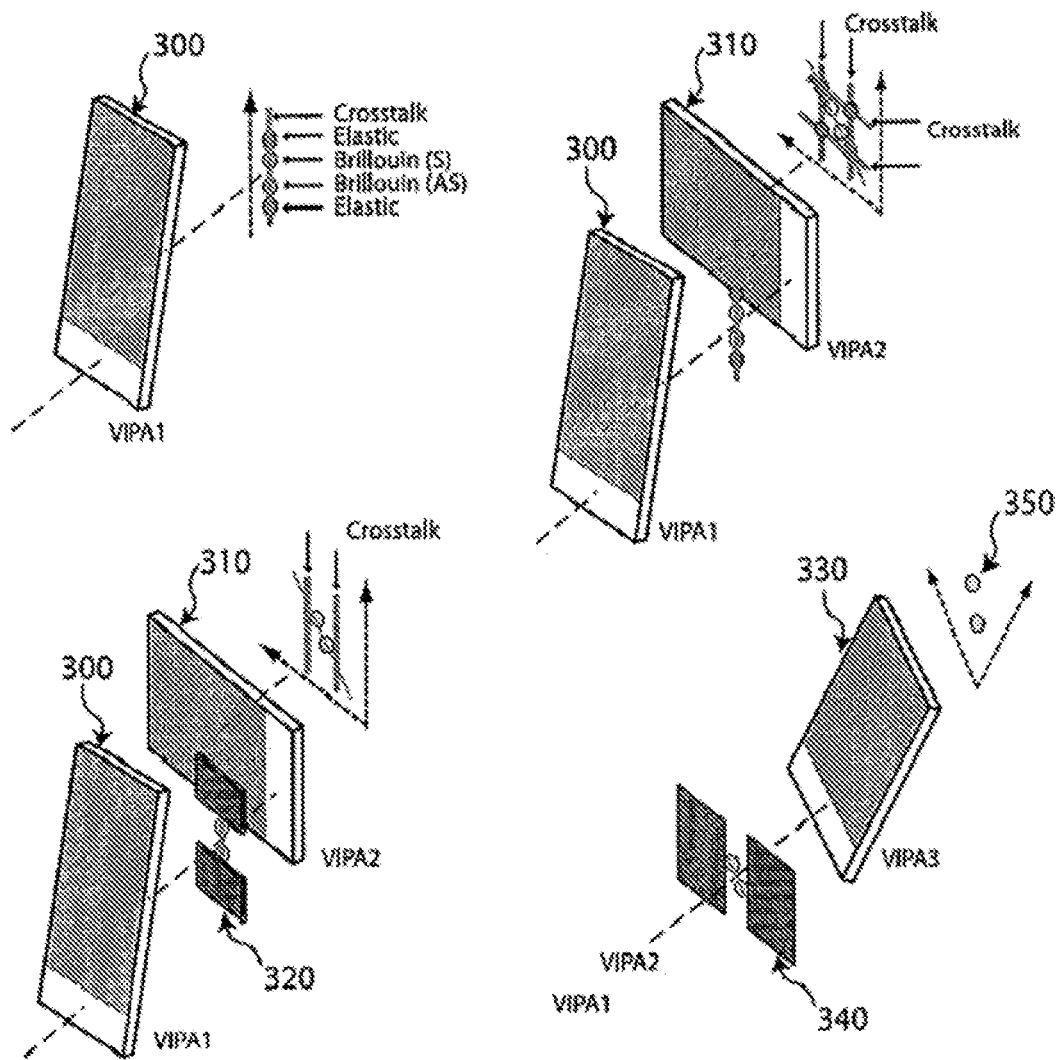
FIG. 3 illustrates a schematic of an exemplary configuration and principle of a spectrometer consisting of multiple VIPA etalons cascaded in the cross-axis configuration.

Cascading two or more VIPAs is a viable option to increase contrast without hurting significantly the sensitivity of the spectrometer. A single VIPA etalon 300 produces spectral dispersion along one spatial direction, parallel to its coating direction, while leaving unchanged the optical beam propagation in the direction perpendicular to its coating direction. Multiple single VIPA etalons can be cascaded in such a way that each VIPA's orientation matches the spectral dispersion axis from the previous stage interferometer. FIG. 3 illustrates the principle of cross-axis cascading. The VIPA 300 in the first stage is aligned along the vertical direction and the spectral pattern is dispersed vertically. When the sample is not transparent or when there are strong optical reflections, the elastic scattering component increases dramatically. If the ratio between elastic scattering, (dark green circles) and Brillouin scattering (light-green circles) exceeds the spectral extinction of the spectrometer, a crosstalk signal appears along the spectral axis (green line). This "stray light" can easily overwhelm the weak Brillouin signal.

In a two-stage VIPA, the second etalon 310 is placed orthogonally to the first one 300. The spectral pattern exiting the first stage enters the second etalon through the input window. Both etalons disperse light, in orthogonal directions, so the overall spectral axis of the two-stage device lies along a diagonal direction, at 135° from the horizontal axis if the etalons have identical dispersive power. The second etalon 310 will separate Brillouin signal from crosstalk because, although spatially overlapped after the first stage, their frequencies at each spatial location are different. So, after the second stage, while the Brillouin spectrum lies on a diagonal axis, crosstalk components due to the limited extinctions of the etalons are separated and mostly confined to the horizontal and vertical axis.

Besides spatial separation of signal and stray light, the two-stage spectrometer also allows selective spectral filtering. An appropriate aperture mask 320 can be placed at the focal plane of the first VIPA 300, where a highly resolved spectral pattern is formed. Examples of the mask 320 are a slit or a rectangular aperture. This mask allows unwanted spectral components to be blocked and only the desired portion of the spectrum to pass to the second VIPA 310. For optimal performance, it is often desirable to maintain only two Brillouin peaks (Stokes and anti-Stokes from two adjacent orders) and have a vertical mask cut off all elastic scattering peaks. This greatly reduces crosstalk in the second-stage VIPA 310 and helps avoid saturation of the pixels in a CCD camera placed afterward, which are illuminated by strong unfiltered elastic scattering light.

This cross-axis cascade can be extended to a third stage. In a three-VIPA spectrometer, a third VIPA 330 is oriented perpendicular to the spectral axis of the preceding two stages, so that the Brillouin spectrum can enter through the input window of the VIPA 330. A second mask 340 is employed to further reduce crosstalk. Due to the combined dispersion of the three etalons, the overall spectral axis is further rotated, at about 170° if all the etalons have the same dispersive power.

Following the same cascading principle, a multiple VIPA interferometer of N stages can be built. The k-th VIPA is oriented at an appropriate angle to accept the spectrum dispersed through the preceding k−1 stages. The building block of each stage is modular, comprised of a cylindrical lens $C_k$, an etalon $VIPA_k$, a spherical Fourier transform lens $S_{kf}$ with focal length as mask and a spherical relay lens $S_{k,k+1}$ of focal length $f_{k,k+1}$.

In the first stage, the VIPA is oriented along the direction v1 at an angle $\theta_1$ with respect to the horizontal axis ($\theta_1=90°$ in our experiment), and its spectral dispersion direction, d1, is parallel to v1 with $\psi_1=\theta_1$. In the double-VIPA interferometer, the second etalon is aligned along v2 at an angle $\theta_2=\psi_1\pm\pi/2$, perpendicular to the spectral direction of the first stage d1 ($\theta_2=180°$ in our experiment). After the two etalons, the spectrum emerges at an angle $\psi_2$ along spectral dispersion direction, d2. In a three-stage interferometer, the third VIPA must be oriented perpendicular to d2, at an angle $\theta_3=\psi_2\pm\pi/2$. This arrangement results in a final dispersion direction s3 at an angle $\psi_3$.

For each stage, the dispersion angle, $\phi_k$, imposed on a beam of wavelength $\lambda_k$ by the $k^{th}$ VIPA interferometer was previously derived in both plane-wave and paraxial approximations. The focal length $f_k$ of the spherical lens, $S_{kf}$, after the VIPA determines the linear dispersion power, $s_k$, of the $k^{th}$ stage: $s_k=\phi_k*f_k$. Since telescopes are used to link two subsequent VIPA stages, the overall linear dispersion also depends on the magnifications introduced by such optical systems. Namely, each $k^{th}$ stage introduces a magnification $M_k=f_k/f_{k-1}$ on the spectral pattern obtained by the previous k−1 stages, so that the effective linear dispersion, $s'_k$, due to the $k^{th}$ stage is given by: $s'_k=s_k*M_N*M_{N-1}* \ldots *M_{k-1}$. Therefore, along the overall spectral axis, the total linear dispersion, $S_N$, of an N-stage multiple VIPA interferometer is calculated to be: $S_N=\mathrm{sqrt}(\Sigma_1^N s'^2_k)$, which suggests a theoretical improvement in spectral resolution. When all the spectral dispersions are equal, i.e. $s'_1=s'_2= \ldots =s'_N \equiv s$, the total dispersion becomes $S_N=\sqrt{N}\cdot s$.

Knowing the spectral dispersion and the optical magnification introduced by each stage, the overall dispersion axis can be computed. It can be shown:

$$\psi_{k+1}-\psi_k=\tan^{-1}(s'_{k+1}/S_k)\to\tan^{-1}(1/\sqrt{k}); \quad (7)$$

$$\theta_{k+1}-\theta_k=\tan^{-1}(s'_k/S_{k-1})=\tan^{-1}(1/\sqrt{k-1}). \quad (8)$$

Here, the expressions marked with arrows apply in the case equal dispersion and unit magnification for all stages.

In terms of extinction, a single VIPA spectrometer has extinction, C proportional to its finesse squared: $C\sim 4F^2/\pi^2$, for an input beam with Airy profile. After N VIPA etalons of equal finesse F, the spectral extinction or contrast improves, in principle, to: $C\sim(4F^2/\pi^2)^2$.

We experimentally compared the extinction performance of single-stage, two-stage and three-stage VIPA spectrometers by coupling the single mode laser light directly into the spectrometer and placing a CCD camera in the focal planes of $S_{1f}$, $S_{2f}$ and $S_{3f}$, respectively. To overcome the limited dynamic range of the CCD, we recorded the spectrum at various optical power levels, with calibrated neutral density (ND) filters of optical densities in the range from 0 to 7. Subsequently, the full dynamic range spectrum was reconstructed by rescaling the recorded raw spectra according to the respective attenuation levels. The single-stage VIPA shows an extinction level of about 30 dB over a wide frequency range between 5 and 2.5 GHz. The extinction is improved to 55 dB with two stages and to nearly 80 dB with three VIPA etalons in the middle of the frequency range. It might be possible to improve the extinction up to 90 dB by minimization of aberrations in the optical system and improvements of beam shape or profile.

Figure 4A:
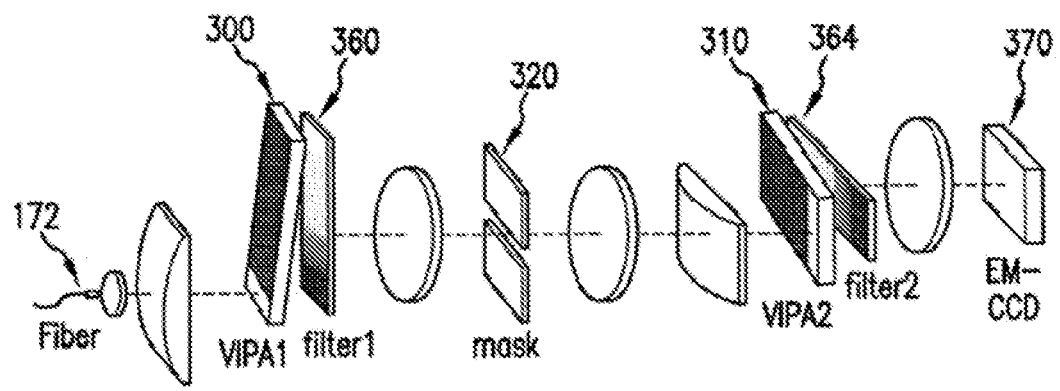
FIG. 4A is a schematic of exemplary two-stage VIPA spectrometer.

Besides the cross-axis cascading, another approach to improve the extinction ration of a VIPA etalon is to make the intensity profile of the VIPA output close to a Gaussian shape, a technique known as apodization. FIG. 4A shows an embodiment of a spectrometer using apodized VIPA etalons. In this embodiment, a spatial filter 360 with a spatially varying transmission profile is used just after the first VIPA etalon 300. The filter 360 converts the otherwise exponential beam profile to a rounded shape, such as a truncated Gaussian profile. After the second VIPA etalon 310, another linear variable filter 365 is employed. The spectrally dispersed output is then imaged on to a detection unit 370. The detection unit is typically a two-dimensional camera based on charge-coupled device (CCD) or a linear detector array.

Figure 4B:
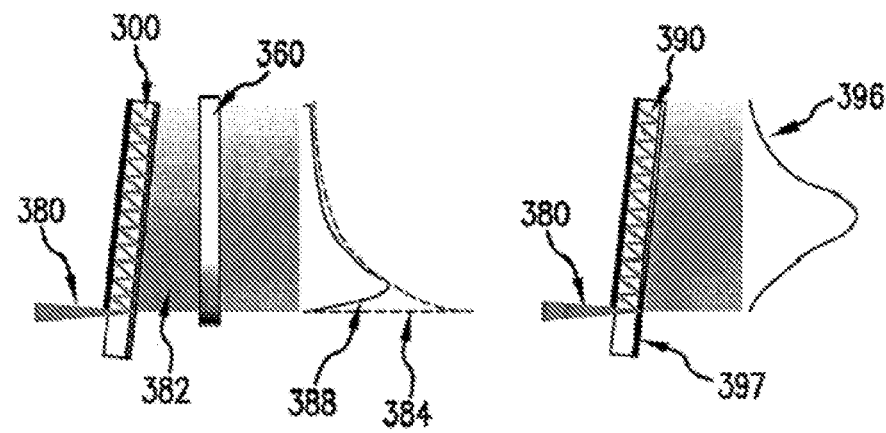
FIG. 4B illustrates the design and output beam profiles in two exemplary apodization schemes.
Figure 4C:
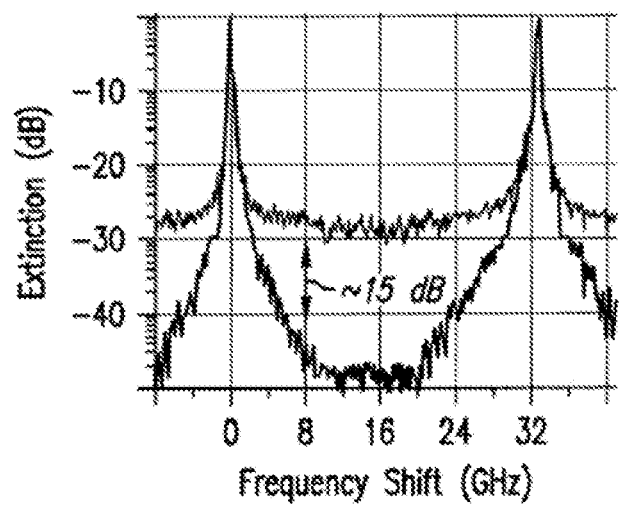
FIG. 4C is a graph of an exemplary Brillouin shift of an epidermal layer in hydrated conditions according to exemplary embodiments of the present disclosure.

FIG. 4B illustrates the role of the apodization filter 360. An input light 380 enters the etalon 300 and is converted to an output beam 380 consisting of a phased array. Normally, in the absence of the filter 360, the intensity of this output beam 380 has an exponential profile 384. The transmission profile of the filter 360 may have a linear, exponential, or more complex nonlinear gradient along the length. The variable filter 360 with an appropriately designed transmission profile converts the exponential profile 384 to a more round, Gaussian-like profile 388. Passing through a Fourier-transform lens in front of the detection unit 370, the rounded profile produces significantly less crosstalk or higher extinction ratio than conventional VIPA etalons. With a linear variable filter, an extinction ration of greater than 40 dB is typically achievable.

In another embodiment of apodization, a VIPA etalon 390 is made with a gradient coating on the exit surface 394, such that its reflectivity and transmission is varied spatially, producing a rounded, Gaussian-like intensity profile 396. For example, with a single VIPA with its reflectivity of the coating 394 is linearly varied from 99.9% to 90%, an extinction ratio of approximately 59 dB can be achieved in principle assuming a constant phase profile. Gradient reflectivity generally results in a spatially varying phase profile. A linear phase chirp may not affect the extinction much and can be compensated for by employing a wedge. With 15 evaporated coating layers, the reflectivity can be made to vary from 92% to 98.5 over 15 mm along the surface 394 can yield a lambda/100 deviation from a wedge. With more layers, a higher reflectivity gradient from 92% to 99.5% can be achieved at the expense of increased nonlinear phase variation of about lambda/40.

Figure 5A:
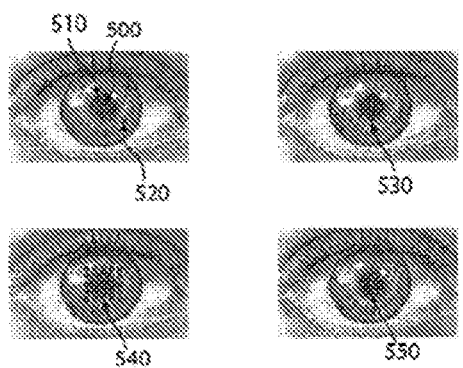
FIG. 5A illustrates a schematic and principle of a single-VIPA spectrometer configured to interrogate multiple spatial locations in the eye simultaneously.
Figure 5B:
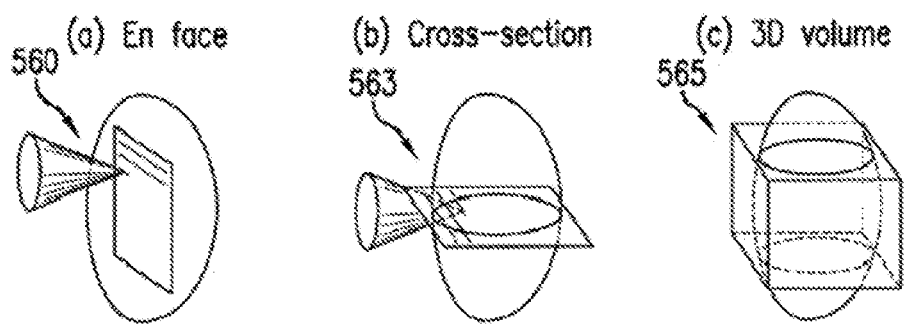
FIG. 5B illustrates a schematic and principle of a single-VIPA spectrometer using a line-focused probe beam.
Figure 5C:
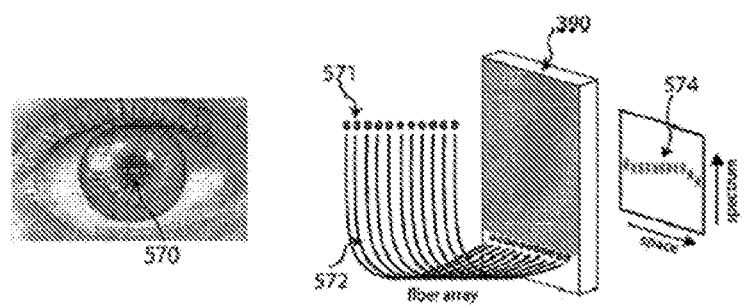
FIG. 5C is a schematic diagram and an image illustrating an exemplary principle of a single-VIPA spectrometer configured to interrogate multiple spatial locations in the eye simultaneously; according to exemplary embodiments.
Figure 5D:
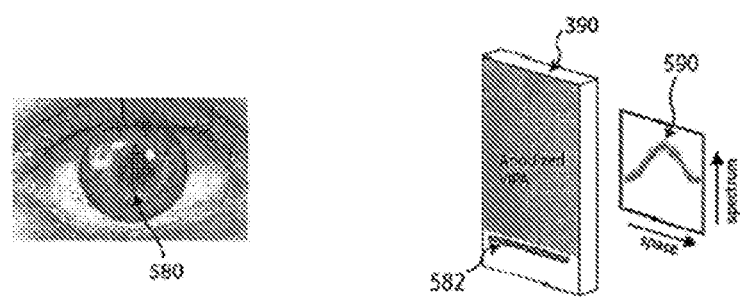
FIG. 5D is a schematic diagram and an image illustrating an exemplary principle of a single-VIPA spectrometer that uses a line-focused probe beam according to further exemplary embodiments.

The system arrangement can be configured to interrogate multiple spatial points simultaneously in the ocular tissues. FIGS. 5A and 5B illustrate two examples. A multiple foci 400 of the probe light are formed, and the Brillouin scattered light 402 from each focus is relayed and coupled to the VIPA etalon 390 through free space or a fiber array 410. The spatio-spectral pattern 420 projected on the detection unit is then processed to provide the biomechanical information about the ocular tissue interrogated.

Another method to interrogate multiple spatial points is to use a line focus 430. The Brillouin scattered light 432 produced from the line focus 430 is relayed and coupled to the etalon 390. The spatio-spectral pattern 420 projected on the detection unit is used to generate the information about the ocular tissues.

Other spectral modalities such as Raman and fluorescence spectroscopy can be performed simultaneously with Brillouin spectroscopy. The combined modalities could provide more comprehensive information about the biochemical and structural as well as biomehcanial and physiological properties of ocular tissues. Since fluorescence, Raman and Brillouin spectrum occupy different region of the electromagnetic spectrum, the second arrangement 150 may be configured to separate these spectra and analyze them simultaneously. Using various spectral dispersive elements, such as gratings and dichroic mirrors, the spectra associated with different emission mechanisms can be easily separated and analyzed. The separated spectra can be projected onto a single detection unit such as a CCD camera after proper equalization of their intensities. Alternatively, the spectra can be directed to different detection units.

We conducted a proof-of-principle experiment and feasibility study of the present description. We developed two prototype instruments consisting of a light source, imaging optics, a spectrometer, and a computer. The light sources for the two prototypes are a frequency-doubled diode-pumped Nd-YAG laser emitting a 532-nm wavelength with a linewidth of 1 MHz and a grating-stabilized single longitudinal mode laser diode emitting at 780 nm with a linewidth of about 100 MHz. Light is focused on a sample through a 35 mm or a 11 mm focal length lens. In the prototypes, we used a beam scanner and a motorized translation stage to move the sample. We employed the epi-detection configuration so that scattered light is collected through the same lens. A single mode fiber was used as confocal pinhole.

Light is then coupled into the VIPA spectrometer for high spatial separation of the spectral components in the plane of an Electron-Multiplied CCD camera. The spectrometer employed a 3 nm bandpass filter to block fluorescence light. The optical design used for the prototype is a combination of a two-stage VIM spectrometer and a variable attenuation neutral density filter. The spectrometer features a spectral resolution of about 1 GHz, an extinction ratio of about 75 dB, and a total insertion loss of 7 dB with a finesse of about 40.

Figure 6A:
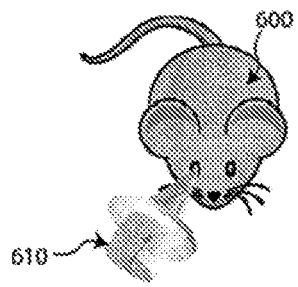
FIG. 6A shows an exemplary schematic of animal imaging.
Figure 6B:
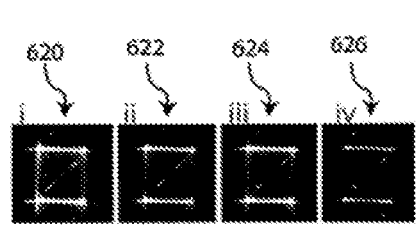
FIG. 6B shows typical experimental data of Brillouin spectra obtained with a two-state VIPA spectrometer at four different locations in a murine lens in vivo: i, aqueous humor; ii, cortex; iii, nucleus; and iv, vitreous humor.
Figure 6C:
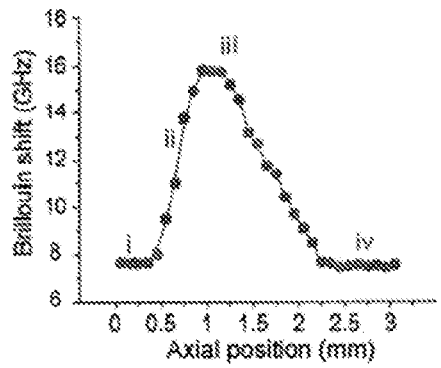
FIG. 6C shows an experimentally obtained, axial profile of the Brillouin frequency shift from the murine lens.
Figure 6D:
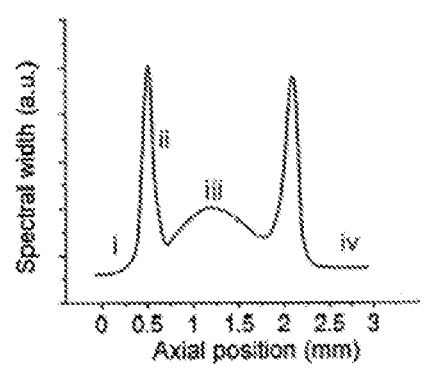
FIG. 6D illustrates an axial profile of the Brillouin linewidth.

To test the possibility of measuring the lens elasticity in vivo, we performed Brillouin imaging on laboratory mice 500 (C57BL/6 strain), as illustrated in FIG. 6A. We focused the probe beam 510 into the eye of the mouse under anesthesia. As the animal was moved by a motorized stage, the optical spectrum of scattered light was recorded. FIG. 6B shows unprocessed data recorded by the camera in the spectrometer at different depths along the ocular optic axis of the lens, featuring the spectral pattern in the anterior cortex (i), lens nucleus (ii), posterior cortex (iii), and vitreous humor (iv). Each spectrum was acquired in 100 ms. FIG. 6C shows a plot of the Brillouin frequency shift measured as a function of depth in the region spanning from the aqueous humor through the lens to the vitreous. FIG. 6D exemplifies an axial profile of the width of the Brillouin spectrum over depth. From these curves, several diagnostic parameters can be derived, such as the peak Brillouin shift at the center of the nucleus, peak Brillouin linewidth, average frequency shift across the lens, etc.

Figure 6E:
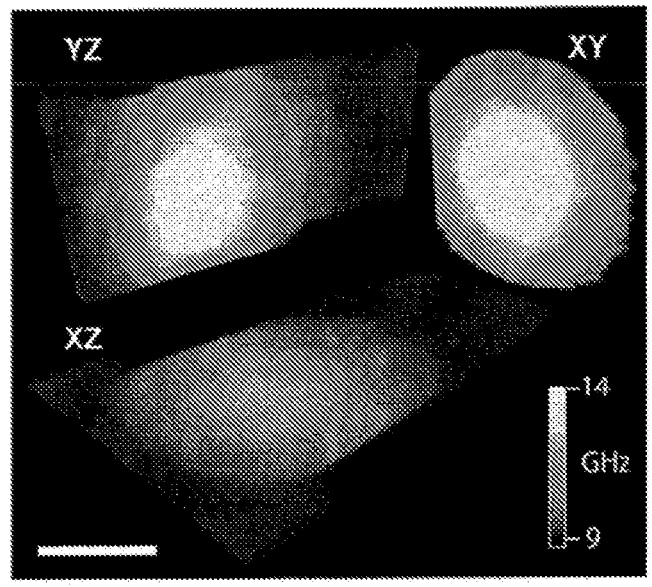
FIG. 6E depicts representative cross-sectional Brillouin images of the murine lens.

FIG. 6E show cross-sectional Brillouin elasticity maps, where the color represents the measured Brillouin frequency shift. The image areas are 1.7×2 mm$^2$ (XY), 1.8×3.1 mm$^2$ (YZ), and 2×3.5 mm$^2$ (XZ), respectively. With a sampling interval of 100 μm, it took ~2 s to scan each axial line (20 pixels), ~50 s for a cross-sectional area (20×25 pixels), and ~20 min over an entire 3D volume. These images visualize the gradient of modulus increasing from the outer cortex to inner nucleus.

Using in vivo Brillouin microscopy, we investigated the natural age dependence of the lens modulus. The peak Brillouin shift observed at the center of the lens nucleus in a mouse at 18 month old was 16 GHz, whereas the shift in a younger mouse at 1 month old was 11.5 GHz. We extended the study to 12 mice of different ages to find an evident trend of age-related stiffening. Next, we imaged one mouse every week for two months and obtained consistent age-related data. Our results indicate a quantitative (linear-log) relationship between the hypersonic elastic modulus and the animal age. This result suggests the first in vivo data evidencing an age-related stiffening, of lenses in mice.

Figure 7A:
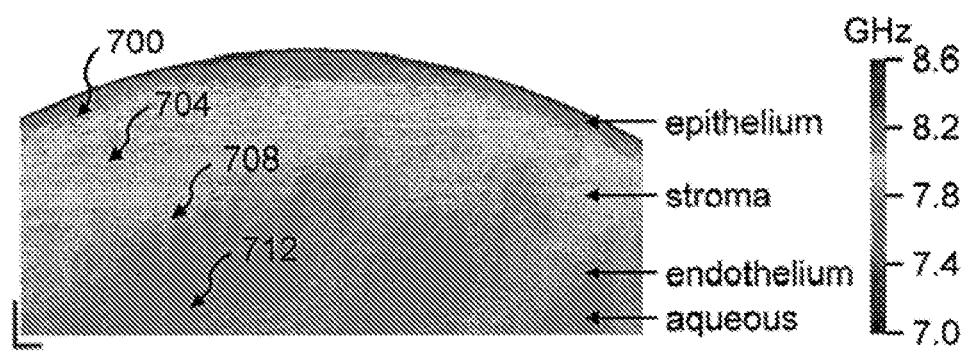
FIG. 7A depicts a cross-sectional Brillouin imaging of a bovine cornea.

We performed Brillouin imaging on bovine eyes ex vivo. FIG. 7A depicts a Brillouin image of the anterior segment of the bovine eye. The transverse and axial resolution of the probe beam was 1 and 5 μm, respectively. The Brillouin frequency shift is encoded in color. The depth-resolved cross-sectional image (XZ) indicates that the Brillouin frequency decreases gradually from the epithelium 600 through the stroma 604 to the endothelium 608. The Brillouin frequency of the aqueous humor 612 is consistent with that shown in FIG. 6C. The variation of the elastic modulus along the depth seems to correlate with the morphological structure of the cornea. The Brillouin modulus doesn't seem to vary much along transverse dimensions in normal cornea. FIG. 78 shows an en face (XY) image of the cornea optically sectioned at a flat plane.

Figure 7B:
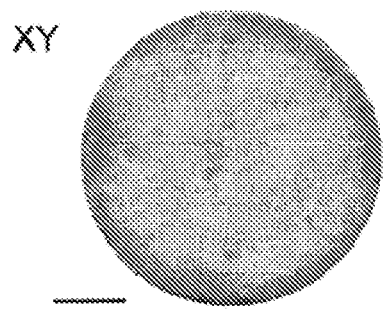
FIG. 7B depicts an en face Brillouin image of the bovine cornea.
Figure 7C:
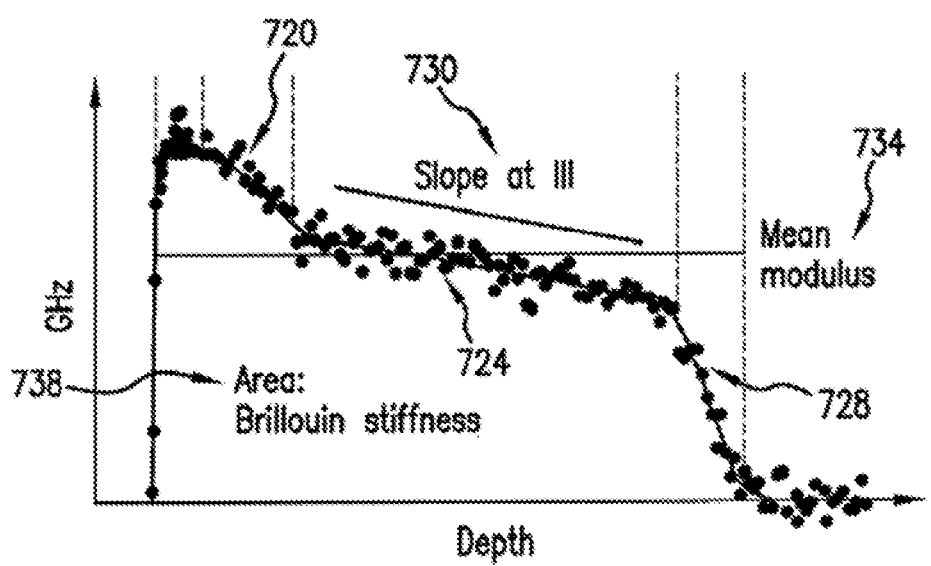
FIG. 7C shows an exemplary axial profile of the Brillouin shift in the bovine cornea.

FIG. 7C shows a laterally averaged axial profile (along the X-axis) obtained from the central 0.5-mm wide portion of the cross-sectional image in FIG. 7A. Several features were observed, such as a steep slope of the Brillouin frequency over depth in the epithelium (620) and the anterior part of stroma, a mild and apparent decreasing slope in the central part (622), and a rapid decreasing slope 624 in the innermost layers of the stroma toward the endothelium).

We can therefore define three slopes (anterior, central and posterior) for each sample that characterize the axial behavior of corneal stiffness. In the anterior region, defined as the depth between 80 and 180 μm, we measured an average slope (620) to be 1.09±0.26 GHz/mm. In the central region, defined as the depth between 300 and 600 μm, we measured the average slope (622) to be 0.36±0.06 GHz/mm. And, in the posterior radon over the depth between 680 and 780 μm, we measured the average slope 624 to be 2.94±0.18 GHz/mm. The difference between the three slope measurements was highly statistically significant with p-values of <0.001 for the three comparisons calculated with unpaired two-tailed t-test. Another characteristic parameter that can be quantified is the mean Brillouin shift 630, or the space average over the entire depth.

Using the infrared prototype system we performed the first in vivo study of cornea and lens in a human subject. We have verified that the features we had seen in animal studies are also present in humans, and the instrument is sensitive to detect the elasticity of human cornea and lens. The axial profile acquired with a continuous-wave power of 0.7 mW shows a decreasing Brillouin frequency from anterior to posterior cornea and a gradual increase in stiffness from the aqueous humor to the lens nucleus.

Figure 8A:
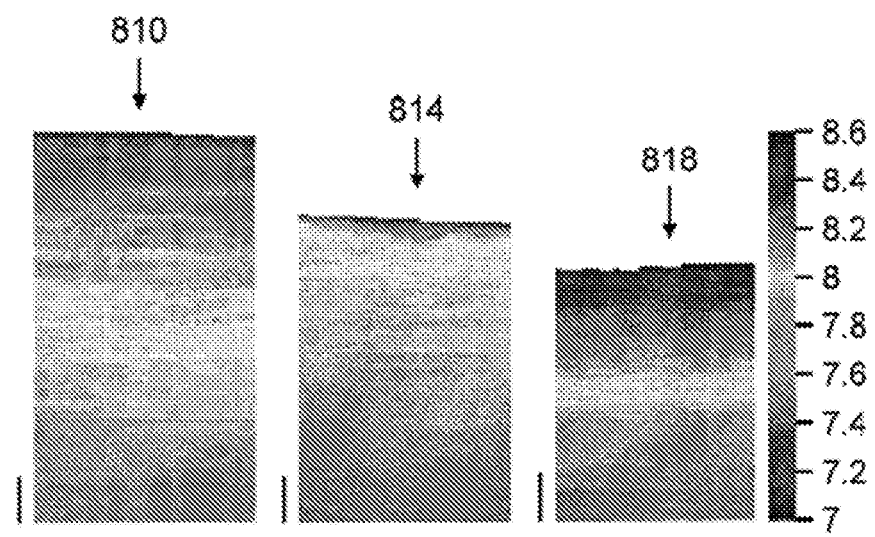
FIG. 8A depicts cross-sectional Brillouin images of a corneal tissue before and after cornea cross-linking.

We tested the potential as a monitoring tool for corneal procedures. We tested if Brillouin biomechanical imaging is sensitive to corneal stiffness changes induced by therapeutic procedures known as corneal collagen crosslinking (CXL). CXL is a promising technique that promotes the formation of covalent bonds between collagen fibers inside corneal stroma through a photosensitizing agent and light irradiation. Enhancing the amount of crosslinks between collagen fibers leads to a stiffer corneal stroma. We performed the CXL procedure on bovine corneal samples. A photosensitizer (Riboflavin) was diffused into the stroma of the cornea after removal of the epithelium and was activated by illuminating blue light. FIG. 8A shows Brillouin cross-sectional images of bovine cornea samples in three different states: intact (left), after removal of epithelium (middle), and after the crosslinking procedure (right). It is apparent that the cross inking procedure greatly has enhanced Brillouin modulus the stroma. Shrinking of tissue after crosslinking is well documented.

Figure 8B:
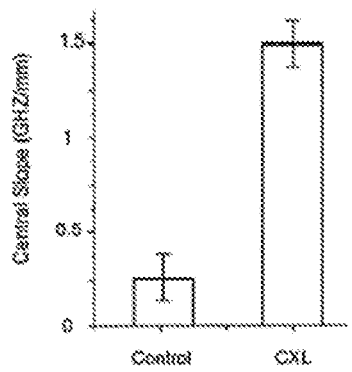
FIG. 8B shows a marked difference between normal and crosslinked cornea tissues in terms of the axial slope of Brillouin shift in the stroma.
Figure 8C:
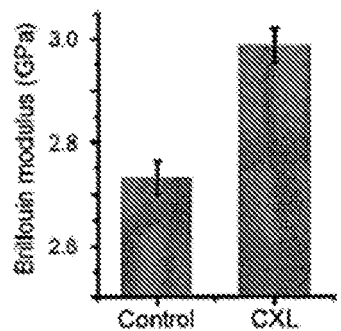
FIG. 8C shows a significant difference in the space-averaged Brillouin modulus between the normal and cross-linked corneal tissues.

Using Brillouin parameters we can quantify the effect of CXL procedure. Using analogous procedure to the one described previously, we obtained corneal axial profiles before and after the CXL. We found that CXL resulted in a dramatic increase in the downward slope (622 in FIG. 7C for a normal tissue) of Brillouin frequency over depth in the stromal region. FIG. 8B shows the increase of the central slope (absolute value) for control versus treated samples (N=4). The difference was statistically significant with a p-value of <0.0001 in unpaired two-tailed t-test. FIG. 8C shows a statistically significant increase of the mean Brillouin modulus averaged along the depth profile. The increase in the treated tissues was about 10%.

Finally, performed Brillouin analysis on surgically extracted human corneas from healthy donors and keratoconus patients undergoing corneal transplants. We found that a statistically significant difference in both the central slope and mean Brillouin modulus.

All of these experimental results indicate the usefulness of this description in clinical and preclinical ophthalmology as well as basic eye research. The Brillouin ocular analyzer may be proven to be a useful diagnostic tool, facilitating early diagnosis, screening of at-risk patients, monitoring therapeutic responses, developing novel approaches for treatment, and understanding pathogenesis.

The mechanical properties of the crystalline lens, sclera, and cornea play an important role in several medical problems, such as cataracts, presbyopia and corneal ectasia. In turn, these disorders and age are known to alter the mechanical properties of the tissues. This description enable us to obtain the information relevant to the biomechanical and physiological states of various tissues in the eye noninvasively in living patients and animals, providing useful information for understanding, diagnosing and treating the medical problems. In this description, the mechanical properties of the ocular tissues are obtained from the spectrum of light reemitted from ocular tissues via Brillouin scattering. This information is useful for diagnosis and treatment of ocular disorders in the clinical settings, as well as in basic and preclinical stages.

The techniques described herein can be used in an algorithm, including algorithms based on numerical analysis, such as finite element analysis (FEA), which uses the local or global Brillouin modulus values. Such numerical analysis enables material information on a localized level to be used, where each element in the FEA model, corresponding to a segment of an ocular component, is able to have individual visco-elastic modulus values assigned. Without such localized material information, elements of an FEA model (e.g., a voxel in a 3D array of elements) may need to assign a single material constant throughout a modeled region, which would not be as useful for dynamically guiding a procedure based on such an FEA model. Even if assigned material constants could be updated based on in-situ measurements, it is still more useful to have a high resolution dynamically evolving model where each individual element is updated based on monitored properties of the ocular component(s). In addition to the Brillouin modulus, other information including geometric information, such as corneal topography, curvature, thickness, physiological information such as intra ocular pressure, and incision parameters can be input to the FEA engine generating the numerical model. The algorithm may generate an output, which may include a stress-strain map or local stress value. The analysis output may be used to simulate varied incisions (e.g. location, length, angle, and depth) and predict the refractive impact of the incisions. The algorithm can provide a biomechanics-based stress-strain maps that can be used in a nomogram to help achieve the desired surgical outcome or refractive result.

Figures 9A, 9B, 9C, 9D, 9E:
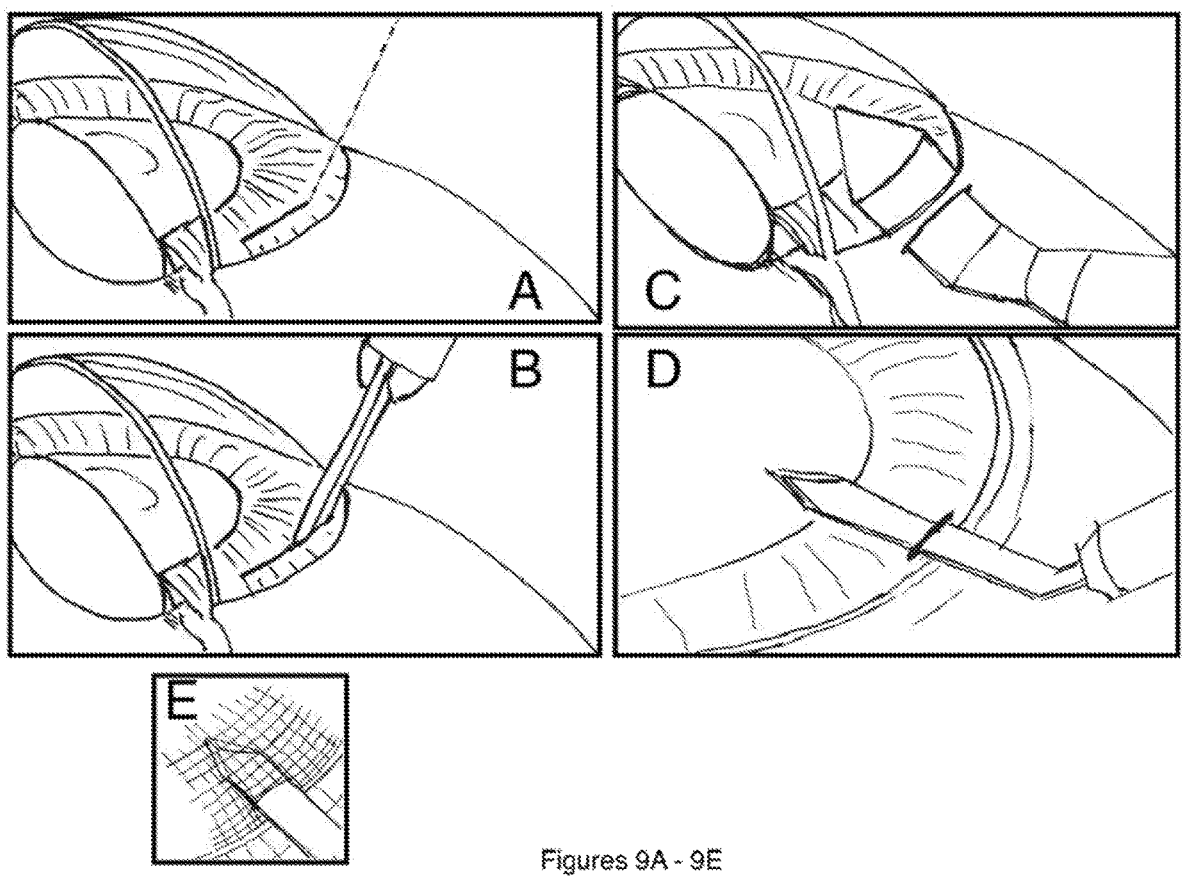
FIGS. 9A-9E depict exemplary incisions that can be guided.

FIGS. 9A-9E depict exemplary incisions that can be guided using the techniques described herein. FIGS. 9A and 9B depict incisions into the cornea with a laser and a mechanical means, respectively. FIG. 9C shows an incision into the sclera, which can have an effect on the corneal structure. FIG. 9D depicts a limbal relaxing incision (LRI). FIG. 9E shows the damnation of the finite element model mesh of the cornea at the location of the incision.

There may be challenges that need to be overcome to obtain the peripheral measurements of the cornea. A measurement instrument can be configured to make it easier and/or more efficient to take such measurements, either in a specific system for peripheral measurements or in a system that can toggle between central measurements and peripheral measurements. For example, an oblique angle at which the treatment laser is incident can be taken into account.

Aspects of the techniques described herein can be applied to Brillouin scanning measurement of modulus or stiffness of sclera for diagnosis and prognosis of a condition, such as myopia or glaucoma, for example, to optimize the treatment pathway for that condition.

The sclera also known as the white of the eye, is the opaque, fibrous, protective, outer layer of the eye containing collagen and elastic fiber. In humans the whole sclera is white, contrasting with the colored iris. Changes in the shape of the eye have been shown to contribute to the development of myopia. Investigation has also been performed to determine if or by how much scleral compliance or stiffness contributes to the development and progression of myopia. Corneal contribution of compliance/stiffness has been said to be small. Axial myopia is attributed to an increase in the eye's axial length. Curvature myopia is attributed to the curvature of one or more refractive surfaces of the eye, especially the cornea. In the case of either axial myopia or curvature myopia, it is unclear bow properties of the sclera influence the curvature and/or irregularity of the refractive surfaces of the eye. Studies in the field have examined how properties such as thickness of ocular tissues, may statistically differ between high myopes and emmetropic healthy controls. Some studies claim that the development and progression of myopia is due to an increase of vitreous chamber depth, which may be related to elongation of the sclera or scleral ectasia. Although the definition of pathologic myopia has not been standardized, the commonly used criteria for pathologic myopia include myopic refractive error (spherical equivalent (SE)) greater than 6.00 D or 8.00 D or an axial length greater than 26.5 mm.

Myopia may also be closely linked with sclera deformation, and sclera biomechanics has been speculated to be a factor for predicting myopia. Despite known treatment pathways, pathologic or progressive myopia patients comprising approximately 4% of myopic population still have not optimized treatment pathways. Myopia treatment includes vision correction through glasses, contact lens, refractive surgeries, and medical therapy with atropine. In vivo high spatial resolution measurement of the elastic modulus of sclera is now enabled by the techniques described herein.

The techniques described herein use the measurement of Brillouin scattering to assess biomechanical properties of the sclera and other ocular components, which facilitates potential prognosis for developing conditions including axial myopia, curvature myopia, and pathological myopia. In certain embodiments, local Brillouin modulus is taken both from the surface of the sclera and within the sclera. Reflectivity of the sclera can be taken into consideration requiring the setup described in the Appendix to be modified according to a number of potential parameters, including the wavelength of the light source and extinction of the spectrometer. Also, since the sclera scatters light relatively strongly (in comparison to the cornea, crystalline lens, and vitreous), accessing Brillouin modulus from inside of the sclera, at varying depths, is a challenge. Potential approaches to overcome this include the use of Brillouin spectrometer instrument with sufficiently high extinction ratio, typically over 65 dB or ideally over 80 dB, to reduce the elastic scattering from the sclera. The scattering in the sclera is wavelength dependent. A spectral range above 1000 nm in wavelength or around 1300 nm or 1550 nm may be advantageous because the reduced scattering from the sclera. Additional embodiments may include an optical probe, which may employ a waveguide or a fiber-optic setup, for delivering the probe light to the sclera and capture the Brillouin scattered signal from the sclera.

Additional embodiments may include one or more Brillouin measurements of the sclera, at varying surface or depth locations or both, may be combined through numerical methods, for example, as averages or ratios to create a scleral biomechanics (e.g., a coefficient). Such a coefficient may be compared to and numerically combined, through a variety of methods, with other biomechanics measures taken from additional ocular tissues, including but not limited to the cornea. The measurements can include an array of simultaneous or non-simultaneous measurements.

In embodiments that jointly measure and assess biomechanical properties of the sclera and the cornea, the ratio or comparison between different measures from these two tissues may be particularly useful because it may provide insights to how the deformation of corneal or scleral tissues, and the transitional zone between sclera and cornea and conjunctiva (which covers the sclera up to the cornea) and cornea, will progress over time. Not only progression over time, but also assessment of the status of this zone can help to better understand keratoconus, ectasia and other corneal irregularities. The techniques described herein can also be used to measure the stiffness of conjunctiva, a thin layer around sclera to provide additional stiffness, and feedback into the algorithm to determine the progression of myopia, corneal disorders and irregularities, or even pre-disposition for ectasia and keratoconus.

In other embodiments, local Brillouin modulus is taken both from within the crystalline lens, which facilitates potential guidance for treatments of the crystalline lens, for example, in conjunction with presbyopia or extraction of the crystalline lens in case of cataract surgery.

Brillouin microscopy can also be used to measure the propagation speeds and damping coefficient of not only longitudinal but also transverse acoustic waves. From the measured data, the anisotropic mechanical or visco-elastic properties of tissues can be determined. For each measurement, the polarization states of Brillouin scattered light with respect to the polarization state of the input light, and also with respect to the symmetry axis of the sample, can be determined. For example, the symmetry axis can be the orientations) of collagen fibers in the cornea. For such isotropic samples, by symmetry no transverse (shear) acoustic modes should be detectable in the back scattering geometry. When the axis is tilted, symmetry is broken and the shear waves can be measured. For this measurement, the input light is typically polarized by using a linear, or circular, polarizer, and the scattered light is detected through a polarization sensitive detector containing, for example, one or more polarizers and/or polarization splitters. The instrument may also employ an arrangement to vary the relative orientation of the beam axis with respect to the sample. The arrangement may include a beam tilt probe.

The techniques can also be applied to other procedures. The biomechanical information from the cornea and/or sclera can provide information that is useful to determine patient-specific optimal protocols for intervention. The intervention or treatment of myopia includes scleral crosslinking or drugs such as atropine.

Measurements of the bulbar sclera can be part of the monitoring of scleral crosslinking or impact of drugs such as atropine.

Measurement of the posterior sclera might be possible by accessing the sclera through the pupil non-invasively to monitor the same processes.

Monitoring of various ocular components can be useful to guide not only noninvasive but also invasive procedures such as vitreo-retinal procedures like pars-plana vitrectomy or retinal laser treatments to name a few.

Other embodiments are within the scope of the following claims.

What is claimed is:

1. An apparatus for performing a procedure based on monitored properties of at least one ocular component of an eye, comprising:
    at least one first arrangement configured to perform a procedure on at least one section of a first ocular component of the eye;
    at least one second arrangement configured to provide at least one first electromagnetic radiation to the at least one section of the first ocular component so as to interact with at least one acoustic wave in the first ocular component, wherein at least one second electromagnetic radiation is produced based on the interaction;
    at least one third arrangement configured to receive multiple portions of the at least one second electromagnetic radiation, each portion having been emitted from a different corresponding segment of the at least one section of the first ocular component; and
    at least one fourth arrangement configured to monitor a visco-elastic modulus of the at least one section of the first ocular component based on the multiple portions during the procedure performed on the at least, one section of the first ocular component;
    wherein the first arrangement is further configured to apply feedback to the procedure based least in part on the monitored visco-elastic modulus, including at least one of: (1) guiding a trajectory of an incision based on different respective monitored values of visco-elastic modulus for the segments, or (2) determining a number of incisions to be made based on different respective monitored values of visco-elastic modulus for the segments.

2. A method for performing a procedure based on monitored properties of at least one ocular component of an eye, comprising:
    performing a procedure on at least one section of a first ocular component of the eye;
    providing at least one first electro-magnetic radiation to the at least one section of the first ocular component so as to interact with at least one acoustic wave in the first ocular component, wherein at least one second electromagnetic radiation is produced based on the interaction;
    receiving multiple portions of the at least one second electro-magnetic radiation, each portion having been emitted from a different corresponding segment of the at least one section of the first ocular component;
    monitoring a visco-elastic modulus of the at least one section of the first ocular component based on the multiple portions during the procedure performed on the at least one section of the first ocular component; and applying feedback to the procedure based at least in part on the monitored visco-elastic modulus, including at least one of: (1) guiding a trajectory of an incision based on different respective monitored values of visco-elastic modulus for the segments, or (2) determining a number of incisions to be made based on different respective monitored values of visco-elastic modulus for the segments.

3. The method of claim 2, wherein the procedure uses an optical source to provide a third electro-magnetic radiation to the at least one section of the first ocular component.

4. The method of claim 2, wherein the procedure uses an acoustic source to provide at least a portion of the energy in the acoustic wave.

5. The method of claim 2, wherein the numerical analysis comprises finite element analysis.

6. The method of claim 2, wherein monitoring the visco-elastic modulus of the a least one section of the first ocular component includes detecting the portions of the at least one second electro-magnetic radiation using a polarization sensitive device to determine characteristics of the portions of the at least one second electro-magnetic radiation that are associated with propagation direction of the acoustic wave.

7. The method of claim 2, wherein monitoring the visco-elastic modulus of the at least one section of the first ocular component includes detecting each of the portions of the at least one second electro-magnetic radiation in a different location of a two-dimensional sensor array.

8. The method of claim 2, wherein the visco-elastic modulus is determined for each of a plurality of the segments, and is represented a parameter that includes a component representing a viscous modulus and a component representing an elastic modulus.

9. The method of claim 2, wherein the procedure comprises procedure that increases stiffness of the first ocular component.

10. The method of claim 9, wherein the procedure that increases stiffness of the first ocular component comprises collage crosslinking of a cornea of the eye.

11. The method of claim 2, further comprising:
performing the procedure on at least one section of a second ocular component of the eye;
providing a portion of the at least one first electro-magnetic radiation to the at least one section of the second ocular component so as to interact with at least one acoustic wave in the second ocular component, wherein at least one third electro-magnetic radiation is produced based on the interaction; receiving multiple portions of the at least one third electro-magnetic radiation, each portion having been emitted from a different corresponding segment of the at least one section of the second ocular component; monitoring a visco-elastic modulus of the at least one section of the second ocular component based on the multiple portions of the at least one third electromagnetic radiation during the procedure performed on the at least one section of the second ocular component; and
applying feedback to the procedure based at least in part on the monitored visco-elastic modulus of the at least one section, of the second ocular component;
wherein the multiple port ions of the at least one second electro-magnetic radiation are received through a spectrometer configured to have a first extinction efficiency that isolates a spectral characteristic of the at least one second electro-magnetic radiation, and the multiple portions of the at least one third electro-magnetic radiation are received through the spectrometer configured to have a second extinction efficiency that isolates a spectral characteristic of the at least one third electro-magnetic radiation.

12. The method of claim 11, wherein the second extinction efficiency is greater than the first extinction efficiency, the number of received portions of the at least one third electro-magnetic radiation is lower than the number of received portions of the at least one second electro-magnetic radiation, and the time over which each portion of the at least one third electro-magnetic radiation is received is longer than the time over which each portion of the at least one second electro-magnetic radiation is received.

13. The method of claim 12, wherein the first ocular component is a cornea of the eye, and the second ocular component is a sclera of the eye.

14. The method of claim 2, wherein the procedure comprises a procedure that reduces stiffness of the first ocular component.

15. The method of claim 14, wherein the first ocular component comprises a crystalline lens of the eye, and the procedure that reduces stiffness of the first ocular component comprises laser induced optical breakdown of the crystalline lens.

16. The method of claim 14, wherein the procedure that reduces stiffness of the first ocular component comprises an incision.

17. The method of claim 16, wherein applying feedback to the procedure based at least in part on the monitored visco-elastic modulus includes determining a number of incisions to be made based on different respective monitored values of visco-elastic modulus for the segments.

18. The method of claim 16, wherein the incision comprises a laser incision that induces optical breakdown of the first ocular-component based on cavitation bubble creation.

19. The method of claim 16, wherein the incision comprises a mechanical incision that induces mechanical breakdown of the first ocular component.

20. The method of claim 16, wherein applying feedback to the procedure based at least in part on the monitored visco-elastic modulus includes guiding a trajectory of the incision based on different respective monitored values of visco-elastic modulus for the segments.

21. The method of claim 20, wherein guiding the trajectory includes determining at least one of: a radius of curvature of at least a portion of the trajectory, or a length of the trajectory.

22. The method of claim 2, wherein the at least one second electro-magnetic radiation is produced based on a Brillouin scattering interaction.

23. The method of claim 22, wherein applying feedback to the procedure includes guiding the procedure over the at least one section based on different respective monitored values of visco-elastic modulus for the segments.

24. The method of claim 22, wherein applying feedback to the procedure includes applying real time feedback to guide the procedure in real time.

25. The method of claim 24, wherein guiding the procedure in real time includes determining a plurality of values of visco-elastic modulus for the segments based on different respective values of a spectral characteristic of each of the multiple portions of the at least one second electro-magnetic radiation in less than 0.4 seconds.

26. The method of claim 23, wherein a monitored value of visco-elastic modulus for a particular segment is determined based at least in part on at least one of a spectral line width or spectral shift of a spectrum of a corresponding portion of the at least one second electro-magnetic radiation.

27. The method of claim 23, wherein the segments are distributed in three spatial dimensions to provide anisotropic monitoring of the visco-elastic modulus.

28. The method of claim 23, wherein a monitored value of visco-elastic modulus for each of the multiple segments is computed based on a numerical analysts that provides a time-dependent evolution of a spatial-dependent function, of multiple discrete element values, where each discrete element value is derived, from a monitored value of visco-elastic modulus for at least one of the multiple segments, and each discrete element value is updated at each of multiple sequential times during the procedure.

\* \* \* \* \*

UNITED STATES PATENT AND TRADEMARK OFFICE
CERTIFICATE OF CORRECTION

PATENT NO. : 10,952,608 B2
APPLICATION NO. : 15/548264
DATED : March 23, 2021
INVENTOR(S) : Jang Lawrence Hyun Yoo et al.

It is certified that error appears in the above-identified patent and that said Letters Patent is hereby corrected as shown below:

In the Specification

Column 13, Line 2, "X and V" should be --X and Y--.

Column 15, Line 18, Eq. (8), "$\theta_{k+1} - \theta_k = \tan^{-1}(s'_k / S_{k-1}) = \tan^{-1}(1 / \sqrt{k-1})$," should be --$\theta_{k+1} - \theta_k = \tan^{-1}(s'_k / S_{k-1}) \to \tan^{-1}(1 / \sqrt{k-1})$--.

Column 17, Line 64, "FIG. 78" should be --FIG. 7B--.

Column 18, Line 14, "posterior radon over" should be --posterior region over--.

Column 18, Line 48, "modulus the" should be --modulus in the--.

Column 19, Line 58, "damnation" should be --deformation--.

Column 20, Line 19, "unclear bow properties" should be --unclear how properties--.

Signed and Sealed this
Fourth Day of May, 2021

Drew Hirshfeld
*Performing the Functions and Duties of the
Under Secretary of Commerce for Intellectual Property and
Director of the United States Patent and Trademark Office*